United States Patent [19]

Santamaria et al.

[11] Patent Number: 5,424,184
[45] Date of Patent: Jun. 13, 1995

[54] DNA SEQUENCE-BASED HLA CLASS I TYPING METHOD

[75] Inventors: Pedro Santamaria, Minneapolis; Michael T. Boyce-Jacino, Saint Paul; Jose Barbosa, Roseville; Stephen S. Rich, Saint Paul; Anthony J. Faras, Long Lake, all of Minn.

[73] Assignee: Regents of the University of Minnesota, Minn.

[21] Appl. No.: 697,421

[22] Filed: May 8, 1991

[51] Int. Cl.[6] .................. C12Q 1/48; C12Q 1/68; C12N 15/11; C07H 21/04
[52] U.S. Cl. .................................... 435/6; 435/15; 435/91.2; 435/91.21; 536/24.33; 935/8; 935/17; 935/18; 935/77; 935/78
[58] Field of Search .................. 435/6, 15, 91, 91.2, 435/91.21; 536/27, 24.33; 935/8, 17, 18, 77, 78

[56] References Cited

U.S. PATENT DOCUMENTS

| | | | |
|---|---|---|---|
| 4,582,788 | 4/1986 | Erlich | 435/6 |
| 4,683,195 | 7/1987 | Mullis et al. | 435/6 |
| 4,683,202 | 7/1987 | Mullis | 435/91 |
| 4,835,098 | 5/1989 | Orr et al. | 435/6 |

FOREIGN PATENT DOCUMENTS

| | | |
|---|---|---|
| 3927467 | 2/1991 | Germany . |
| 4006974 | 9/1991 | Germany . |
| WO89/11547 | 11/1989 | WIPO . |

OTHER PUBLICATIONS

*Biotechniques*, vol. 7, No. 4, issued Apr. 1989, K. B. Gorman et al., "Simplified Method for Selective Amplification and Direct Sequencing of cDNAs", pp. 326-329, see entire document.

*Journal of Immunology*, vol. 142, No. 11, issued 01 Jun. 1989, P. Parham et al., "Diversity and Diversification of HLA-A,B,C Alleles", pp. 3937-3950, see entire document.

*Clinical Chemistry*, vol. 35, No. 11, issued Nov. 1989, L. J. McBride et al., "Automated DNA Sequencing Methods Involving Polymerase Chain Reaction", pp. 2196-2201, see especially pp. 220-2201.

Marsh et al., "Nomenclature for factors of the HLA system, 1989", *Immunogenetics*, 31:131 (1990).

F. Bach et al., "The HLA class II genes and products: the HLA-D region", *Immuno. Today*, 6:89 (1985).

R. Zinkernagel et al., "Restriction of *in vitro* T cell-mediated cytotoxicity in lymphocytic chloriomeningitis within a syngeneic or semiallogeneic system", *Nature*, 248:701 (1974).

F. Bach et al., "The Major Histocompatibility Complex-Genetics and Biology", *New Eng. J. of Med.*, 295:806 (1976).

Bidwell, "DNA-RFLP analysis and genotyping of HLA-DR and DG antigens", *Immunology Today*, 9:18 (1988).

J. Tiercy et al., "Identification and distribution of three serologically undetected alleles of HLA-DR by oligonucleotide-DNA typing analysis", *Proc. Natl. Acad. Sci. USA*, 85:198 (1988).

P. Erlich, *PCR Techniques*, (1989).

Todd et al., "HLA-DQ gene contributtes to susceptibility and resistance to insulin-dependent diabetes mellitus", *Nature*, 329:599 (1987).

Saiki et al., "Enzymatic Amplification of -Globin Genomic Sequences and Restriction Sittte Analysis for (List continued on next page.)

*Primary Examiner*—Robert A. Wax
*Assistant Examiner*—Rebecca Prouty
*Attorney, Agent, or Firm*—Barbara Rae-Venter

[57] ABSTRACT

The present invention provides a process for determining genotypes in highly polymorphic systems by polymerase chain reaction amplification of cDNA or genomic DNA and direct sequencing polymerase chain reaction products using oligonucleotide primers. More specifically, Class I HLA genotypes can be unambiguously determined in any subject in 16-24 hours by direct sequencing of HLA-A, HLA-B, and HLA-C transcripts enzymatically amplified and sequenced using a limited number of selected oligonucleotides.

14 Claims, 10 Drawing Sheets

OTHER PUBLICATIONS

Diagnosis of Sickle Cell Anemia", *Science*, 230: 1350 (1985).

K. Mullis et al., "Specific Synthesis of DNA *in Vitro* via a Polymerase-Catalyzed Chain Reaction", *Methods Enzymol.*, 155:335 (1987).

Saiki et al., "Analysis of enzymatically amplified -globin and HLA-DQA DNA with allele-specific oligonucleotide probes", *Nature*, 324:163 (1986).

Scharf et al., "Direct Cloning and Sequence Analysis of Enzymatically Amplified Genomic Sequences", *Science*, 233:1076 (1986).

Gyllenstein et al., "Generation of single-stranded DNA by the polymerase chain reaction and its application to direct sequencing of the HLA-DQA locus", *Proc. Natl. Acad. Sci USA*, 85:7652 (1988).

Narang et al., "Improved Phosphotriester Method for the Synthesis of Gene Fragments", *Methods Enzymol.*, 68:09 (1979.

Brown et al., "Chemical Synthesis and Cloning of a Tyrosine tRNA Gene", *Meth. in Enzymol.*, 68:109 (1979).

Caruthers et al., "Chemical Synthesis of Deoxyoligonucleotides by the Phosphoramidite Method", *Methods Enzymol.*, 154:287 (1987).

Schulhof et al., "The final deprotection stepin oligonucleotide synthesis is reduced to a mild and rapid ammonia treatment by using labile base-protecting groups", *Nucl. Acid Res.*, 15:397 (1987).

Dupont, *Hum. Immunol.*, 26:3 (1984).

Chirgwin et al., "Isolation of Biologically Active Ribonucleic Acid from Sources Enriched in Ribonuclease", *Biochemistry*, 18:5247 (1979).

Gough, "Rapid and Quantitative Preparation of Cytoplasmic RN from Small Numbers of Cells", *Anal. Biochem*, 173:93 (1988).

Knowles, *Immunobiology of the HLA*, vol. I, 365-380 (1989).

Gregerson et al., *Proc. Nat'l Acad. Sci.*, 83, 2642-46 (1986).

Kao et al., *J. Immunol.*, 142, 1743 (1989).

Merryman et al., *Immunol.*, 140, 2447-52 1988).

Merryman et al., *J. Immunol.*, 143, 2068-73 (1989).

S. Marsh et al., "HLA-DRB nucleotide sequences, 1990", *Immunogenetics*, 31:141 (1990).

Johns et al., "Purification of Human Genomic DNA from Whole Blood Using Sodium Percholorate in Place of Phenol", *Anal. Biochem.*, 180:276 (1989).

R. Higuchi, "Simple and Rapid Preparation of Samples for PCR", *PCR Technology*, (1989).

Marsh et al., *Immunogenetics*, 31:131 (1990).

Terasaki et al. "Microdroplet Assay of Human Serum Cytotoxins", *Nature*, 204:998 (1964).

Anasetti et al., "Effect of HLA Incompatibility on Graft-versus-Host Disease, Relapse, and Survival after Marrow Transplantation for Patients with Leukemia or Lymphoma", *Hum. Immonol.*, 29:70 (1990).

Yang, *Immunobiology of HLA*, I:332 (1989).

P. Parham, *Nature*, 350, 111 (1991).

G. Nepom, *Immunol. Res.*, 8, 16 (1989).

E. Stoflet et al., *Science*, 239, 491 (1988).

G. Thomson, *The Handbook of Experimental Immunology*, 3, Chapter 102 (1986).

L. Smith et al., *The Handbook of Experimental Immunology*, 3, Chapter 87 (1986).

U. B. Gyllenstein et al. "Generation of single-stranded DNA by the Polymease Chain Reaction and its application to direct sequencing of the HLA-DQA locus". Proc. Natl. Acad. Sci 85:7652-7656 (Oct. 1988).

M. A. Innis et al. "DNA Sequencing with Thermus aquaticus DNA Polymerase and direct sequencing of Polymerase Chain Reaction Amplified DNA". Proc. Natl. Acad. Sci. 85:9436-9440 (Dec. 1988).

Wong, C. et al. "Characteristics of B-thalassemia mutahins . . . " Nature 330:384-386.

Gorman, K. B. et al. "Simplified Method for Selective . . . " Biotechniques 7(4) 326-392 (Apr. 1989).

Parham, P. et al. "Diversity and Diversification of . . . "J. Immunology 142(11)3937-3950 (Jun. 1989).

McBride, L. J. "Automated DNA Sequencing Methods . . . " Clinical Chemistry 35(11)2196-2201 (Nov. 1989).

Engelke, D. R. "Direct Sequencing of anzymahically . . . " Proc. Natl Acad. Sci. 85:544-548 (Jan. 1988).

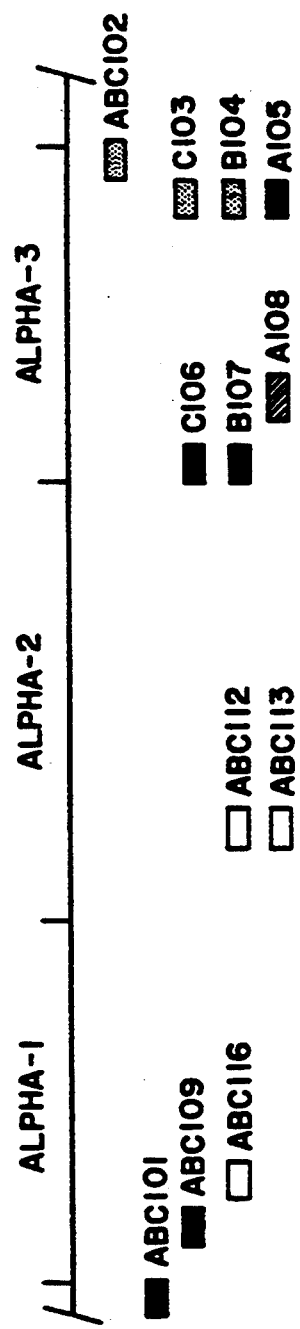

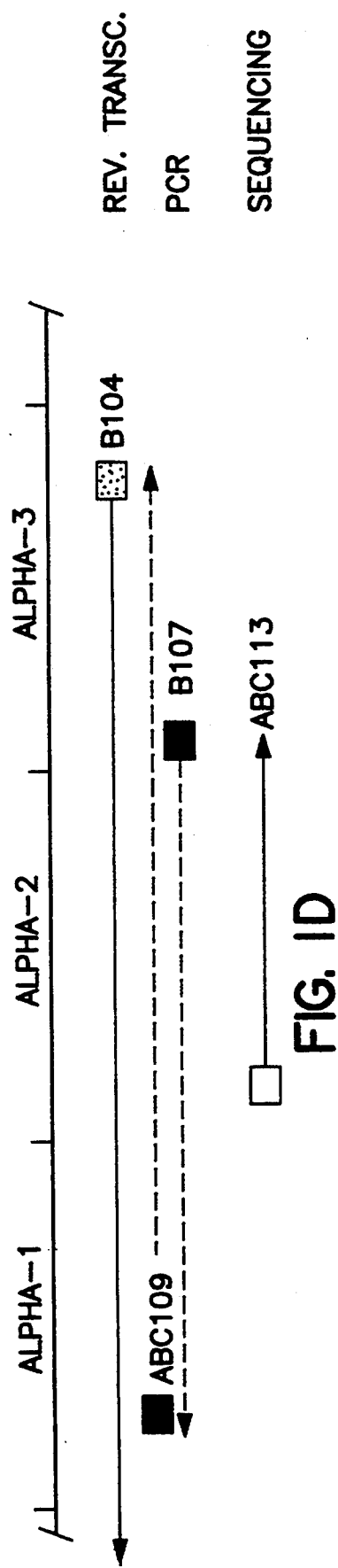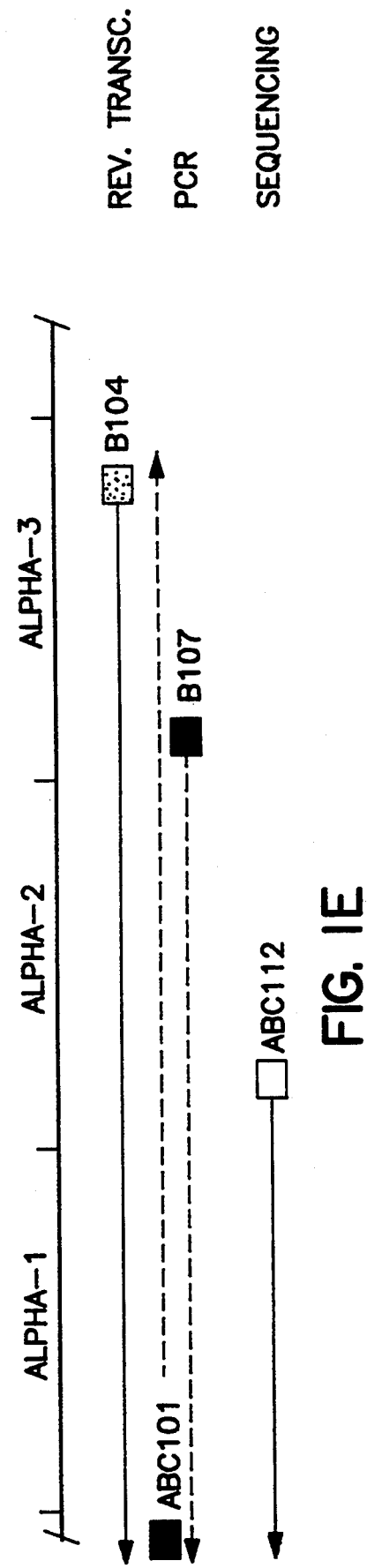
FIG. 1D
FIG. 1E

DNA SEQUENCE-BASED HLA CLASS I TYPING METHOD

This invention was made with Government support under grant number DK 36828 by the U.S. National Institutes of Health. The Government has certain rights in the invention.

TECHNICAL FIELD

The present invention relates to a process for determining genotypes of highly polymorphic systems, such as the Class I genes of the major histocompatibility complex of humans. Specifically, the method of the present invention involves amplifying the alleles carried by any given individual at a gene locus or loci of interest by polymerase chain reaction with selected oligonucleotide primers. The polymerase chain reaction products are directly sequenced followed by evaluation of the resulting nucleic acid ladders to determine the genotype of sample nucleic acid.

BACKGROUND OF THE INVENTION

HLA Class I Polymorphism Analysis.

1. Introduction

The major histocompatibility complex (MHC) includes the human leukocyte antigens (HLA) gene complex which is located on the short arm of human chromosome six. These genes encode cell-surface proteins which regulate cell-cell interactions of the immune response. The various HLA Class I loci encode the heavy chain of the Class I molecules (44,000 dalton polypeptide), which associate with B-2 microglobulin. The different Class I dimers are expressed on the surface of essentially all human cell types. These molecules are involved in the presentation of endogenous peptides (i.e., virally-encoded proteins) by the expressing cells; this molecular complex is recognized on the target cells by cytotoxic T lymphocytes, in a self-restricted manner.

The HLA-A, -B and -C loci of the HLA Class I region exhibit an extraordinarily high degree of polymorphism. The WHO nomenclature committee for factors of the HLA system [Marsh and Bodmer, Immunogenetics, 31:131 (1990)] designated 25 alleles at the HLA-A (HLA-A,0101, A*0201, etc.), 32 alleles at the HLA-B, and 11 alleles at the HLA-C loci. Since this high degree of polymorphism relates to the function of the HLA molecules, much effort has gone into designing accurate and optimal methods for detecting the many possible alleles that may be carried at each locus by any given individual of the population. Products of the HLA genes were first identified by reactions of antisera. Serological techniques remain the primary, and in many cases the only, typing method for HLA antigens. The complement-dependent cytotoxicity (CDC) assay is the method most often used to define serologic specificities [Terasaki and McClelland, Nature, 204:998, (1964)]. The advantages of the CDC include the small volumes of antisera and target cells and the relatively short time required for the test.

One great disadvantage of serological typing is that alloantisera are not infrequently limited in number and volume, and often have complex reactivities, so that an extensive program is required to identify and obtain useful sera. Perhaps most importantly, however, many cellularly and/or biochemically defined polymorphisms, which in all likelihood have functional significance in bone marrow transplantation, cannot be detected by serological techniques [Anasetti et al., Hum. Immunol., 29:70 (1990)].

One-dimensional isoelectric focusing (1D-IEF) is very effective in identifying serologically undetectable variants or subtypes for the HLA-A and HLA-B antigens [Yang, Immunobiology of HLA, Vol. I, 332 (1989)] which have been implicated in the development of acute graft-versus-host disease and in graft rejection in bone marrow transplantation. In this technique, metabolically labeled cell lysates are immunoprecipitated using monoclonal antibodies to Class I antigens and the immunoprecipitates are desialated and subjected to isoelectricfocusing. The technique, however, is time consuming and cumbersome. Interpretation of the IEF patterns is dependent on prior knowledge of the serological definition, and certain HLA antigens show so many overlapping bands that IEF assignment is difficult and impractical.

It is believed that only about 30% of the existing Class I sequences are known as of today. This limited knowledge extraordinarily complicates the application and use of other molecular approaches for Class I HLA typing which are being used for Class II typing (i.e., oligotyping). Furthermore, because the distribution and nature of the sequence polymorphisms in the Class I genes is very different from that seen in Class II genes, oligotyping strategies for Class I genes may require the use of a very large number of oligonucleotides to type the alleles known at the present time and this number may become much larger as new allelic sequences are described. Application of a sequence-based typing technique to the analysis of HLA Class I polymorphism presented a series of problems additional to those associated with HLA Class II typing. These problems are: 1) the informative polymorphism at Class I loci spans 2 different exons (approximately 600 base-pairs), instead of 1 in Class II genes; 2) the HLA-A, -B and -C loci are believed to be far more polymorphic than Class II loci; 3) the different Class I loci are far more related to each other in terms of DNA and amino acid sequence than Class II loci are to each other. Thus, when the alleles at each locus are compared with each other, they resemble alleles at a single locus and, therefore, given that up to 6 different Class I genes may be expressed by a given individual (2 alleles at each locus) this increases the number of technical limitations to molecular typing imposed by this polymorphic system.

Accordingly, there is a need for a method to determine genomic information from such a highly polymorphic system as the HLA- Class I system that addresses the limitations imposed by previous methods. That is, a system that is capable of determining the nucleotide sequences of the genes carried by any given individual without the need to have previous knowledge of the individual's HLA type as defined by other methods.

The present invention provides a molecular approach for accurate HLA Class I sequence-based typing that is rapid, avoids the use of oligonucleotides specific for each known allele, requires the use of only a small number of oligonucleotide primers, does not require previous typing information, can readily detect new sequence variants unidentifiable with more conventional approaches, and is entirely automatable.

SUMMARY OF THE INVENTION

The present invention relates to a method for determining the nucleic acid sequence of one or more polymorphic genes of a subject by amplifying and direct sequencing genomic or complementary DNA molecules for each allele at each gene locus to be sequenced. The amplification and sequencing of DNA molecules utilizes selected locus-specific oligonucleotide primers that provide for detailed characterization of HLA gene polymorphism, at the sequence level, in the population. The method is specifically designed to provide rapid and accurate determination of a major histocompatibility complex class genotype of a subject in a sample (e.g., Class I). Most particularly, the method is directed to determining at least one HLA Class I gene locus including HLA-A, and/or HLA-B, and/or HLA-C genes.

To determine a Class I gene locus nucleic acid sequence polymorphism with the method of the present invention, nucleic acid (RNA or DNA) from a sample is isolated. According to the present invention, the sample nucleic acid sequence is determined by: amplifying the cDNA molecules or genomic DNA by polymerase chain reaction to generate sufficient product for each allele of each gene locus to be sequenced, with all of the alleles for each gene locus and chromosome to be sequenced being amplified with at least one Class I loci-specific primer annealing to all possible alleles at all Class I loci at each chromosome and a locus-specific primer that anneals preferentially to a region of each said gene locus which has a sequence that is shared by all alleles at said locus; preparing the products of each PCR for sequencing (clean); sequencing directly the products of each polymerase chain reaction product to detect each allele at each gene locus of each chromosome with Taq polymerase and either a locus-specific primer and a Class I loci-specific primer or two Class I loci-specific oligonucleotide primers; and analyzing each sequenced product for each locus and primer combination(s) to determine the genotype of the subject. The analysis is conducted by comparing the nucleotide sequence of each allele of each gene locus sequence to known sequences for each locus. Comparison of nucleic acid ladders for sequenced alleles can be conducted visually or using computer software.

In a preferred embodiment of the present invention the nucleic acid is RNA. When the subject nucleic acid is RNA, prior to amplification, cDNA molecules are synthesized for each allele at each Class I loci of each chromosome to be sequenced using oligonucleotide primers that anneal to a region of each gene locus shared by all alleles of each said gene locus. The unincorporated oligonucleotide primer used for generating the cDNA is then removed.

In a preferred embodiment, the process of the invention is automated for use in rapid genotype determinations, including diagnosis of genetic diseases, forensics and paternity testing. Automation of the process includes isolating the sample nucleic acid with an RNA/DNA extractor; amplifying the synthesized cDNA molecule or the isolated DNA molecule by polymerase chain reaction using a thermocycler to generate the polymerase chain reaction products; sequencing the polymerase chain reaction products in an automated sequencing apparatus; and analyzing each sequenced polymerase chain reaction product with the computer having a database with allelic sequence information and the capacity to conduct the appropriate algorithm for comparing the polymerase chain reaction product sequence for each allele amplified with known gene sequences.

The invention further relates to specific groups of oligonucleotide primers useful in the steps of cDNA synthesis, cDNA amplification by polymerase chain reaction and direct sequencing of the polymerase chain reaction products to determine the nucleotide sequence of each of the alleles at each locus of each chromosome that is amplified. Useful single strand DNA oligonucleotide primers are described in Table 1 herein.

BRIEF DESCRIPTION OF THE DRAWINGS

FIG. 1A shows a schematic of the primer binding sites on HLA-A, HLA-B, and HLA-C transcripts involved in the cDNA/PCR/Sequencing steps for determining HLA Class I (HLA-A, HLA-B and HLA-C) genes. In FIGS. 1A-1D, stippled boxes represent RT primers; black boxes represent PCR primers; blank boxes represent sequencing primers; boxes with horizontal lines represent RT-PCR primers; and boxes with diagonal bars are PCR/seq primers.

FIGS. 1B-1D show primer binding sites on HLA-A, HLA-B and HLA-C transcripts in the method according to the present invention. Each figure shows the end-products of the two reactions for each locus.

DETAILED DESCRIPTION OF THE INVENTION

Figure 1B:
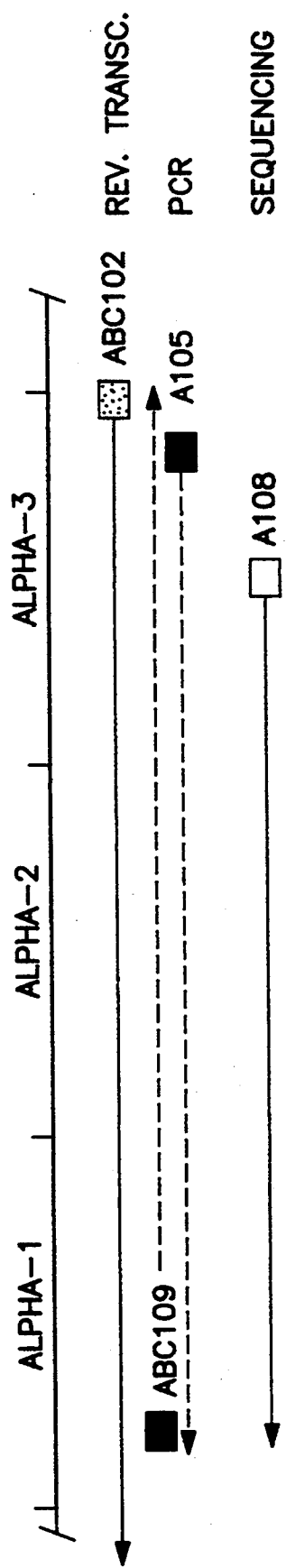
Figure 1C:
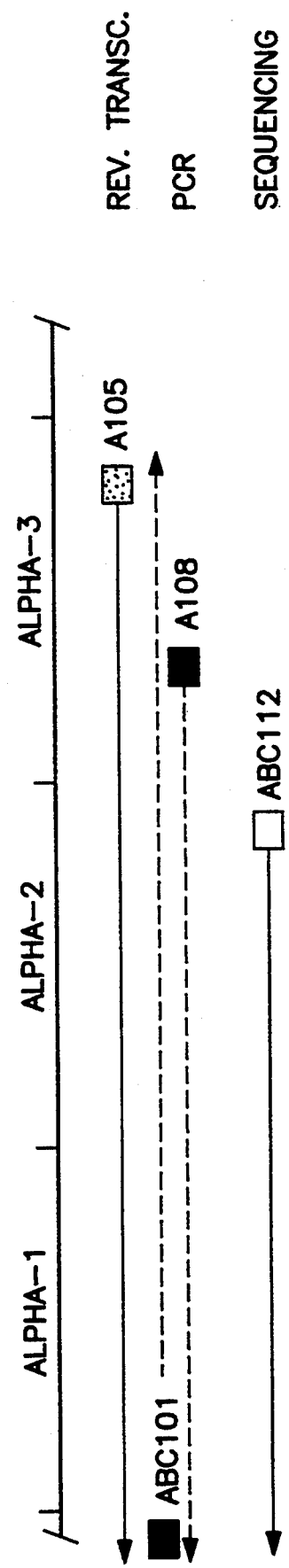
Figure 1F:
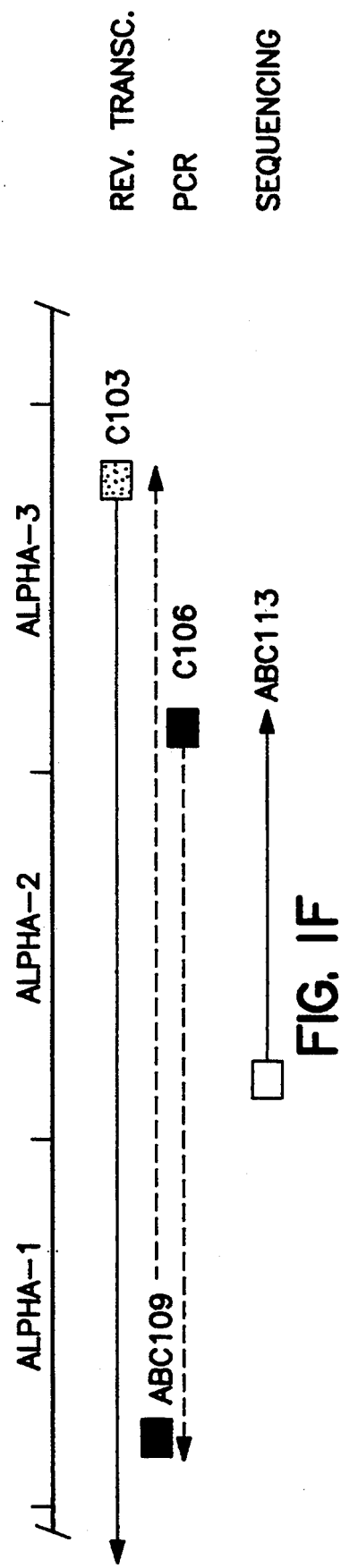
Figure 1G:
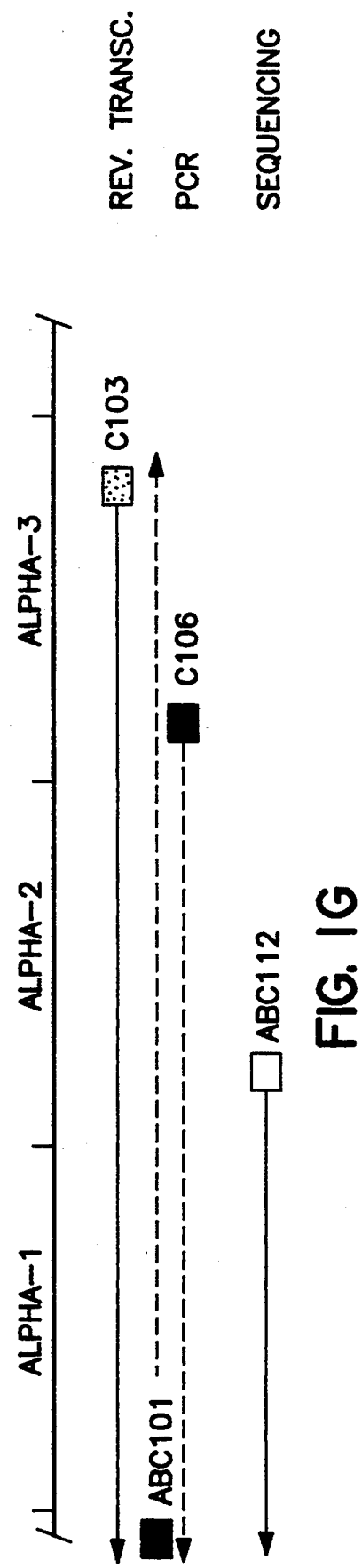

As used herein, the term "gene" refers to a segment of DNA, composed of a transcribed region and a regulatory sequence that makes possible a transcription. The term "gene locus" refers to the specific place on the chromosome where a gene is located. The term "allele" refers to the multiple forms of a gene that can exist at a single gene locus at a single chromosome and are distinguishable from the other possible alleles by their differing effects on phenotype (detectable outward manifestations of a specific genotype). "Haplotype" refers to the specific allele composition of the genes at multiple loci on the same chromosome. As used herein the term "genotype" refers to the specific allelic composition of a gene at multiple linked loci at each chromosome (2 haplotypes).

The term "oligonucleotide" as used herein refers to a molecule having two or more deoxyribonucleotides or ribonucleotides, preferably more than three deoxyribonucleotides. The exact number of nucleotides in the molecule will depend on the function of the specific oligonucleotide molecule. As used herein the term "primer" refers to a single stranded DNA oligonucleotide sequence, preferably produced synthetically which is capable of acting as a point of initiation for synthesis of a primer extension product which is complementary to a nucleic acid strand to be copied or a point of initiation for sequencing a DNA molecule. In the case of primers intended for use in synthesizing cDNA or amplifying cDNA or genomic DNA molecules by polymerase chain reaction products, the length and sequence of the primer must be sufficient to prime the synthesis of extension products in the presence of a polymerization enzyme. Preferably, the length of the primer is from about 5–50 nucleotides, more preferably from about 5–20 nucleotides. Specific length and sequence of the primer will depend on complexity of required DNA or RNA target templates, as well as conditions of primer employment such as temperature, ionic strength, and $MgCl_2$ concentration as well as role of primer in the reaction (cDNA synthesis, PCR or sequencing).

As used herein, "locus-specific oligonucleotide primer" refers to an oligonucleotide molecule that corresponds to a region of high DNA sequence conservation (i.e. less than 1–2 nucleotide variations) among all alleles of a single gene locus. For example, in the case of the HLA-A locus, the locus-specific oligonucleotide primer will anneal or bind preferentially to all HLA-A alleles under the conditions described here. Similarly, HLA-B and HLA-C locus-specific oligonucleotide primers will preferentially bind to HLA-B and HLA-C alleles, respectively. In contrast to this, "Class I loci-specific oligonucleotide primer" refers to an oligonucleotide molecule that corresponds to a region of high DNA sequence conservation (i.e., less than about 1–2 nucleotide variations) among all the individual gene loci of a gene class and anneals to a region of a group of related HLA loci that has the same conserved sequence for all alleles at all the related loci. In the preferred embodiment, the Class I loci-specific oligonucleotide primers anneal or bind to a relatively conserved (i.e., about 1–2 mismatches) region of all alleles of HLA-A, HLA-B, and HLA-C genes. While the Class I loci- or individual locus-specific primer need not correspond exactly to the nucleotide template to which it anneals, as stated above, each primer will have minimal, preferably less than one or two mismatches with the target nucleotide template. Functionally, the Class I loci- and individual locus-specific primers are capable of equally priming the target template (cDNA, PCR product, etc.) at high stringency conditions.

The present invention is directed to a process for determining the sequences of the alleles of highly polymorphic gene systems carried by any given individual, such as, for example, the human HLA system, most particularly Class I genes, using enzymatic amplification and direct sequencing of the gene cDNA molecules using a limited number of primers and avoiding the use of allele specific oligonucleotides as much as possible. The present method is particularly well suited to determining allelic sequences of Class I HLA genes, thereby providing complete HLA Class I genotype information for a subject. Using the method of the present invention complete Class I HLA typing (HLA-A, -B, and -C) can be performed in about 16 to 24 hours or less.

Generally, the method of the present invention involves: extraction of sample nucleic acid; in the case of RNA, generation of cDNA; cDNA or genomic DNA amplification; direct sequencing of amplification products; and analysis of the direct sequence information. Generation of cDNA, amplifying the cDNA and direct sequencing the cDNA amplification products is accomplished using oligonucleotide primers with specific characteristics, such as those described herein.

More specifically, the primers for binding sites on Class I HLA transcripts and cDNA molecules provided in the present invention allow: a) selection of the alleles at each separate locus (A or B or C) and yet allow the detection of both possible alleles at each locus in unknown heterozygotes; and b) generation of sequencing information encompassing both polymorphic exons of Class I genes by using the fewest possible number of reactions.

In the case of RNA, cDNA molecules for each allele at each Class I locus (A or B or C loci) on each chromosome that are to be sequenced are synthesized by employing a locus-specific oligonucleotide primer that anneals to a region of each gene locus which has a sequence that is shared by all the alleles at a given locus (with up to about two nucleotide mismatches between the primer and any allele at that locus) but is different for all the alleles at the other related loci (with at least about two mismatches).

The sample nucleic acid sequence is determined by: amplifying the cDNA molecules by PCR, after removing the unincorporated oligonucleotide primer used for generating the cDNA molecules (clean), to generate sufficient product for each allele of each gene locus to be sequenced, with all of the alleles for each gene locus and chromosome to be sequenced being amplified with at least one Class I loci-specific oligonucleotide primer annealing equally to all possible alleles at each Class I gene loci at each chromosome and a locus-specific oligonucleotide primer that anneals to a region of each gene locus which has a sequence that is shared by all the alleles at the given locus (with up to about two nucleotide mismatches between the primer and any allele at that locus) but is different for all the alleles at the other related loci (with at least about two mismatches); preparing the products of each PCR for sequencing (clean); sequencing directly the products of each PCR product to detect each allele at each gene locus of each chromosome with Taq polymerase and either a locus-specific primer and a Class I loci-specific oligonucleotide primer or two Class I loci-specific oligonucleotide primers; and analyzing each sequenced product for each locus and primer combination(s) to determine the genotype of the subject.

A. Oligonucleotide Primers

The oligonucleotide primers of the present invention can be synthesized using any known suitable method, such as phosphotriester and phosphodiester methods. Narang et al., *Methods Enzymol.,* 68:90 (1979); Brown et al., *Methods Enzymol.,* 68:109 (1979). Oligonucleotides can be prepared using a modified solid support such as a Biosearch 8750 DNA synthesizer. Useful primers can also be isolated from a biological source using appropriate restriction endonucleases which cut double stranded DNA at or near a nucleotide sequence of interest for use as a primer.

B. Extraction of Sample Nucleic Acid

In the process of the present invention any source of nucleic acid can be used as the sample nucleic acid, as long as the sample contains the nucleic acid sequence of interest. For example, the sample chosen for the present method can be RNA, DNA or a DNA/RNA hybrid. While typical samples include peripheral blood mononuclear cells, (PBMNC's), lymphoblastoid cell lines (LCL's), hair cells or the like, for determining human HLA Class I gene polymorphisms LCL's or PBMNC's are preferred. The nucleic acid to be isolated (e.g. RNA or DNA) will depend on the source of genetic material (blood stain, hair, or peripheral blood cells). However, in the case of HLA Class I genes including HLA-A, HLA-B and HLA-C, the preferred isolated nucleic acid is total cellular RNA when the typing is to be done for transplantation purposes or paternity testing. For forensic uses, genomic DNA may be the preferred genetic material in which case different primer considerations would be used. Cytoplasmic and poly(A) +RNA can also be used. It is envisioned that isolation of sample nucleic acid for the present process can be automated using a DNA/RNA extractor (such as Model 341 DNA extractor available from Applied Biosystems, Inc.; Foster City, Calif.).

C. Generation of cDNA

Complementary DNA (cDNA) of the sample nucleic acid is generated using specific oligonucleotide primers and cloned reverse transcriptase following general conditions suggested by the enzyme manufacturer (Bethesda Research Laboratories, Gaithersburg, Md.). Specific differences in type and amount of primers used, dNTP concentrations and elongation times will be readily apparent to those of skill in the art based on the Examples that follow.

D. Polymerase Chain Reaction

Amplification of cDNA or genomic DNA for each gene locus of interest is accomplished using the polymerase chain reaction (PCR) as generally described in U.S. Pat. Nos. 4,683,195 and 4,683,202 to Mullis. The PCR consists of many repetitions of a cycle which consists of: (a) a denaturation step, which melts both strands of a DNA molecule; (b) an annealing step, which is aimed at allowing the primers to anneal specifically to the melted strands of the DNA molecule; and (c) an extension step, which incorporates to the primers deoxyribonucleotides complementary to those of the strand of DNA to which the primers are annealed. The PCR process, as indicated in the Examples, can be conducted using a Thermocycler (Perkin-Elmer, Cetus, Emeryville, Calif.).

The conditions used for the PCR reactions will depend on the specific primers used for a given gene locus application. The concentrations of primers, and buffers used will be apparent from and include the process parameters described in the Examples that follow.

E. Direct Sequencing Of PCR Products

Direct sequencing of double-stranded DNA generated by the PCR is accomplished using Taq polymerase and specific combinations of reagents at appropriate concentrations. The sequencing procedure can be conducted in an automatic sequencing apparatus such as the 373A Model DNA Sequencer from Applied Biosystems Inc. (Foster City, Calif.). The reagents, including sequencing primers, labelled with radioactive or non-radioactive labels, sequencing conditions, and nucleotide termination mixtures will be understood by those of skill in the art based on the direct sequencing procedure specified in the following Examples. The present sequencing protocol for double-stranded PCR templates described here requires the use of specific primers in both the amplification and sequencing steps. The use of specific primer pair combinations is required to generate clean, recognizable sequence ladders corresponding to each locus to be sequenced that can be interpreted.

F. Analysis Of Direct Sequenced PCR Products

The nucleic acid ladders resulting from direct sequencing the cDNA or genomic DNA for each gene locus of interest can be assessed visually from autoradiograms or by employing a computer programmed with nucleotides sequence information for all alleles of all haplotypes and procedures for comparing sequenced alleles and known alleles of gene loci of interest. In a preferred embodiment of the present invention, the evaluation of gene locus alleles involves comparison of the gene sequences of each polymerase chain reaction product with a library of known genotype information such as the information obtained on homologous cell lines very well characterized by methods other than sequencing [Marsh and Bodmer, *Immunogenetics,* 31:131 (1990)] as well as sequences of individual alleles. This comparison can be conducted visually or by computer that generates and compares the specific sequence information for each allele of a gene locus.

It is envisioned that the process of the present invention can be used to amplify and sequence known and unknown highly polymorphic systems (e.g., HLA typing). The method is particularly well suited for Class I HLA typing, reducing its costs, increasing its speed and especially improving its accuracy. The present process is believed to be useful for paternity testing and forensic medicine, with more accuracy than restriction fragment length polymorphism (RFLP), DNA fingerprinting or dot blot-detection systems. While in the latter only a hybridization pattern is observed, direct sequencing of amplified products shows the exact nucleotide sequence of the amplified genes, and hence is more accurate and reliable.

As evidenced by the following Examples, sequence polymorphism analysis of Class I HLA genes can be rapidly performed in any subject of unknown HLA type by means of enzymatic amplification and direct sequencing of Class I genes using a limited number of locus-specific and Class I loci-specific oligonucleotide primer combinations. The approach described herein is entirely automatable using currently available technology and, as opposed to previously described methods using oligonucleotide probes and dot blots, has the advantage of detecting the presence of new allelic sequences or sequence microheterogeneity at the population level. The methodology of the present invention is envisioned to be useful for detailed analyses of the effects of sequence allelism at different Class I HLA loci on graft survival after allogeneic transplantation. The method of the present invention allows rapid and precise sequence analysis of Class I HLA polymorphism in studies of human disease and may be of interest in the search for new Class I sequence variants in large populations of subjects.

concentrated ammonium hydroxide at room temperature for about one hour. The solution containing the partially deprotected oligodeoxyribonucleotide was brought to 65° C. for 16 hours. Ammonia was removed and the residue was subjected to chromatography on a C18 reverse-phase column (RP 304, BioRad, Richmond, Va.) using a linear gradient of 14 to 20% acetonitrile in 0.1 molar ammonium/triethylamine, pH 7.0. The dimethoxytrityle group was removed from the HPLC-purified oligodeoxyribonucleotide by treatment with 70% acetic acid. The detritylated oligodeoxyribonucleotide was recovered by precipitation in ether, vacuum centrifuged until dry, resuspended in water and quantitated by measuring its absorbance at 260 nm.

Using the above procedure, the following oligonucleotide primers corresponding to specified regions of the Class I HLA-A, HLA-B and HLA-C loci were synthesized (see Table I below) and extensively tested:

TABLE I

Oligonucleotides Used for the cDNA/PCR/Sequencing Reactions of Class I HLA Genes

| Sequence Listing No. (Seq) | Primer | | Anneal | Locus (i) | Template | Step |
|---|---|---|---|---|---|---|
| 1 | ABC 101 | 5'-GGCCCTGACCGAGACCTGGGC-3' | −8/−1 | A/B/C | RNA | PCR |
| 2 | ABC 102 | 5'-AGATGGCTCCCATCTCAGGGT-3' | 271–277 | A/B/C | RNA | RT |
| 3 | C103 | 5'-AGGGGCTCTGGCAGCCCCTCG-3' | 270–263 | C | RNA | RT |
| 4 | B104 | 5'-AGGGGCTTCGGCAGCCCCTCA-3' | 270–263 | B | RNA | RT |
| 5 | A105 | 5'-AGGGGCTTGGGCAGACCCTCA-3' | 270–263 | A | RNA | RT/PCR |
| 6 | C106 | 5'-GTCACGTGTGTCTTTGGGTGT-3' | 183–190 | C | RNA | PCR |
| 7 | B107 | 5'-GGTCACATGTGTCTTTGGGGG-3' | 184–190 | B | RNA | PCR |
| 8 | A108 | 5'-AGAGATAGCGTGGTGGGTCAT-3' | 189–195 | A | RNA | PCR/SEQ |
| 9 | ABC109 | 5'-CAGTGGGCTACGTGGACGACA-3' | 24–31 | A/B/C | RNA | PCR/SEQ |
| 10 | ABC116 | 5'-GTCGCTGTCGAACCTCACGAA-3' | 33–39 | A/B/C | RNA | SEQ(alt) |
| 11 | ABC112 | 5'-TTCAGGGCGATGTAATCCTT-3' | 121–127 | A/B/C | RNA | SEQ |
| 12 | ABC113 | 5'-GGCAAGGATTACATCGCCCTG-3' | 120–126 | A/B/C | RNA | SEQ |

The present invention is further described by illustration in the following Examples which are not intended to limit the invention.

EXAMPLE I

1. Preparation of Oligodeoxyribonucleotide Primers and Sequence Primer Combinations Useful for cDNA/PCR/Sequencing Reactions of Class II HLA Genes All of the oligodeoxyribonucleotide primers described herewithin were synthesized as described below:

Automated Synthesis of oligodeoxyribonucleotide primers: The b-cyanoethylphosphoamidites, obtained from Milligen-Biosearch (Novato, Calif.), were sequentially condensed to a nucleoside derivatized controlled pore glass support using a Biosearch 8750 DNA synthesizer. Condensation cycles included detritylation with dichloroacetic acid in dichloromethane, followed by condensation with benzotriazole and capping with acetic anhydride and 1-methylimidazole in tetrahydrofuran and pyridine, with each cycle time being approximately 9 minutes. Yields at each step were >99% as determined by measuring dimethoxytrityle alcohol release. The methodology for oligodeoxyribonucleotide synthesis is described in Caruthers, et al., *Methods Enzymol.*, 154:287 (1987).

Deprotection and purification of oligodeoxyribonucleotide primers: Deprotection and purification of oligodeoxyribonucleotide primers was performed using the procedure described by Schulhof et al., *Nucl. Acids Res.*, 15:397 (1987). Briefly, the oligodeoxyribonucleotide was removed from the solid support by exposure to 2. Combinations of Primers for cDNA/PCR/Sequence Reactions There are specific combinations of oligonucleotide primers for each reaction and for each locus, including cDNA synthesis, PCR amplification and direct sequencing, which are designed to provide all the necessary sequence information for obtaining highly accurate, fast and inexpensive typing results. These combinations are listed in Table II below. Each of these combinations of oligonucleotides is characterized by its ability to generate an end-product (sequencing ladder) which is suitable of being accurately read by the naked eye or processed by computer operated under appropriate software.

For typing purposes in the clinical setting, such as in transplantation, the method uses RNA isolated from peripheral blood mononuclear cells as starting material; for forensic purposes, however, DNA is often the only available template on which amplification and sequencing primers can be employed. The specific combinations of primers for RNA analysis are described below in more detail. The general overview of the HLA typing strategy employing these primer combinations is shown in FIGS. 1(A–D) and 2 and discussed further in Example 2.

TABLE II

Combinations of Primers for cDNA/PCR/Seq Reactions

| Locus | cDNA* | PCR1 | PCR2 | A.T.** | Seq |
|---|---|---|---|---|---|
| (@)1. A | ABC102 | ABC109 | A105 | 55° C. | A108 |
| 2. A | A105 | ABC101 | A108 | 55° C. | ABC112*** |

TABLE II-continued

Combinations of Primers for cDNA/PCR/Seq Reactions

| | Locus | cDNA* | PCR1 | PCR2 | A.T.** | Seq |
|---|---|---|---|---|---|---|
| 3. | B | B104 | ABC109 | B107 | 55° C. | ABC113 |
| 4. | B | B104 | ABC101 | B107 | 55° C. | ABC112*** |
| 5. | C | C103 | ABC109 | C106 | 55° C. | ABC113 |
| 6. | C | C103 | ABC101 | C106 | 55° C. | ABC112*** |

(@) Alternative combination for this reaction: A105 (cDNA), ABC109 (PCR1), A108 (PCR2), ABC113 (Sequencing).
*The RT primer is removed after cDNA synthesis by spin-dialysis.
**The optimal $MgCl_2$ concentration is different for different primer combinations (see below). The concentration ratios between the primers is also different in different reactions (see below).
***Primer ABC116 may be used to sequence these products in order to read polymorphic sequences close to the 5' end of the cDNAs.

EXAMPLE II

Protocol: HLA Class I "Typing" by Direct Sequencing of HLA-A, HLA-B and HLA-C Genes 1. Cell Lines and Subjects Lymphoblastoid cell lines (LCLs) of the 10th International Histocompatibility Workshop [Yang et al., Immunobiology of HLA, Vol I: Histocompatibility Testing 87, (1989); Dupont, Hum Immunol., 26, 3 (1989)] were provided by Dr. Miriam Segall (University of Minnesota). Cell lines were also established on 4 subjects, 3 of them belonging to the same family. All these cell lines had been previously serologically typed for HLA Class I and Class II antigens and were used to test the methodology presented here. The serological types of each of the subjects under study were not known to the investigator performing the sequence analysis at the time the analysis was performed. The cell lines and heterozygote subjects tested included: SA (WS#9001), MZ070782 (9002), JBUSH (9035), JVM (9039), BH (9046), SAVC (9034), DEM (9007), WJR076 (9012), RML (9016), RSH (9021), H0301 (9055), SPOO10 (9036), TF (family 6025-003), KR (family 6044-008), PC (family 6044-005) and AR (6044-006).

2. HLA Class I (A, B and C) Transcript Amplification Using Class I-Specific and Locus-Specific (HLA-A or HLA-B or HLA-C Oligonucleotides Total cellular RNA was prepared from the cell lines by cesium chloride centrifugation [Chirgwin et al., Biochemistry, 18, 5249 (1979)]. One to 5 µg of total cellular RNA was reverse transcribed with Moloney leukemia virus reverse transcriptase (MLVRT) 200µ (Bethesda Research Laboratories) in 50 mM Tris HCl, pH 8.3, 75 mM KCl, 10 mM DTT, 3 mM $MgCl_2$, in the presence of the ribonuclease inhibitor RNAs in (10 units Promega) 75 mM each dNTP in the presence of a limiting amount (5–20 ng) of a locus-specific (A, B and C loci) or a Class I-specific oligonucleotide (A locus) in a 20 µl final volume for 30–45 min. at 37° C. (See Table I for the sequence and specificity of each of the primers and see Table II for the combinations of primers useful for each reaction). FIGS. 1A–1D show a schematic of the cDNA, PCR, and sequencing products generated in each reaction. Note that each pair of reactions proposed per locus generates sequence information from different polymorphic portions of the genes to be sequenced. After the incubation period, the volume of the cDNA synthesis reaction was brought up to 400 µl and spun-dialyzed using Ultrafree-100 columns (Millipore) in order to remove the unincorporated oligonucleotide molecules. The following were added to the retentate (approximately 50 µl): 10 µl of 10X PCR buffer (50 mM KCl, 100 mM Tris-Cl, pH 8.3, 7.5–15 mM $MgCl_2$, 0.1% gelatin), 8 µl of a mixture containing 1.25 mM of each of the four dNTPs, from 3–6 µl of a 25 mM $MgCl2$ solution (the final $MgCl2$ concentration regulates the stringency of the reaction), 75–200 ng of each of two additional oligonucleotides for each reaction (reactions 2, 3, 4, 5, and 6) or 75–200 ng of one primer and 0.75–2 ng of the other primer (reaction 1) and 2 units of Taq polymerase; the final volume was adjusted to 100 µl with distilled water.

The reaction mixture was subjected to 35 cycles of 1 min at 94° C., 1 min at 55° C. and 1 min at 72° C. using a Perkin-Elmer Cetus Thermocycler [see Saiki et al., supra (1985); Mullis and Faloona, Supra (1987); Saiki etal., supra (1986); Scharf et al., supra (1986)]. The primers used, their corresponding sequences and the regions to which they anneal are shown in Table II. The reactions for each locus are performed in separate microfuge tubes (FIG. 2).

Figure 2:
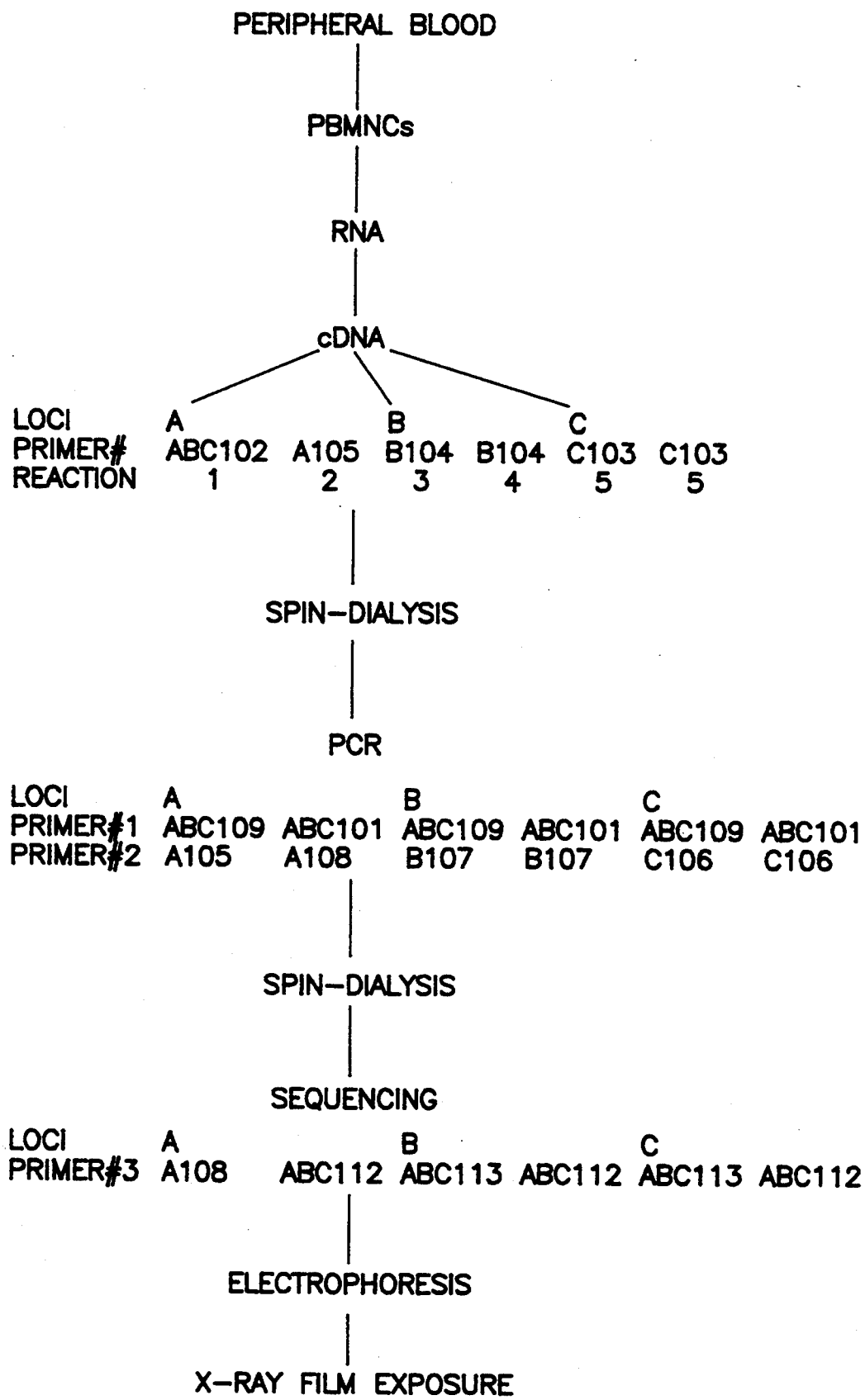
FIG. 2 shows a flow-chart of the procedure for peripheral blood samples. Each reaction is performed in a different test tube. The reactions are named with numbers; these numbers (1-6) correspond to those shown in Table II (combinations of primers/reaction).

Referring to FIG. 2, the specific reaction conditions required in each microfuge tube are as follows:

HLA-A Typing

Reaction 1 (sequencing of 3' end of the alpha2 domain encoding exon of HLA-A).
  a) 10 ng of primer ABC102, 3 microg. of RNA.
  b) spin dialysis.
  c) PCR with 3 microl. of 25 mM $MgCl_2$, 100 ng of primer ABC109, 1 ng of primer A105. 45 cycles (1' at 92° C., 1' at 55° C., 1' at 72° C.).
  d) spin dialysis.
  e) sequencing with primer A108.

Reaction 2 (sequencing of 5' end of alpha2 domain encoding exon and the alpha1 domain encoding exon of HLA-A).
  10 ng of primer A105, 3 microg. of RNA.
  b) spin dialysis.
  c) PCR with 5 microl. of 25 mM $MgCl_2$, 100 ng of primer ABC101, 100 ng of primer A108.
  d) spin dialysis.
  e) sequencing with primer ABC112.

HLA-B Typing

Reaction 3 (sequencing of 3' end of the alpha2 domain encoding exon of HLA-B).
  a) 10 ng of primer B104, 3 microg. of RNA.
  b) spin dialysis.
  c) PCR with 5 microl. of 25 mM $MgCl_2$, 100 ng of primer ABC109, 100 ng of primer B107.
  d) spin dialysis.
  e) sequencing with primer ABC113.

Reaction 4 (sequencing of 5' end of alpha2 domain encoding exon and the alpha1 domain encoding exon of HLA-B).
  a) 10 ng of primer B104, 3 microg. of RNA.
  b) spin dialysis.
  c) PCR with 5 microl. of 25 mM $MgCl_2$, 100 ng of primer ABC101, 100 ng of primer B107.
  d) spin dialysis.
  e) sequencing with primer ABC112.

HLA-C Typing

Reaction 5 (sequencing of 3' end of the alpha2 domain encoding exon of HLA-C).
  a) 10 ng of primer C103, 3 microg. of RNA.
  b) spin dialysis.
  c) PCR with 5 microl. of 25 mM $MgCl_2$, 100 ng of primer ABC109, 100 ng of primer C106.
  d) spin dialysis.
  e) sequencing with primer ABC113.

Reaction 6 (sequencing of 5' end of alpha2 domain encoding exon and the alpha1 domain encoding exon of HLA-C).
  a) 10 ng of primer C103, 3 microg. of RNA.
  b) spin dialysis.
  c) PCR with 5 microl. of 25 mM MgCl$_2$, 100 ng of primer ABC101, 100 ng of primer C106.
  d) spin dialysis.
  e) sequencing with primer ABC112.

The reason for the different ratio of primer concentrations for reaction #1 is that the sequencing primer used to sequence that portion of the HLA-A genes works more efficiently when the limiting primer (0.75–2 ng) is consumed in the reaction. Alternatively, the combination of primers for reaction 1 can be substituted for primers A105 (cDNA), ABC 109 (PCR1), A108 (PCR2) and ABC113 (sequencing) and in this case, 75–200 ng of each PCR primer are used.

2. Direct Sequencing of Amplified Products with Taq Polymerase

The reaction mixture (100 µl) was freed of unincorporated dNTPs and excess of oligonucleotides by spin-dialysis using Ultrafree-100 (Millipore) microconcentrators. Approximately one half of the retentate (20 µl) was dried down and resuspended in 15 µl of 1X Taq sequencing buffer (50 mM Tris-HCl, pH 9, 10 mM MgCl2). Internal oligonucleotides were used for priming the sequencing of HLA-A, HLA-B, and HLA-C genes, respectively (Table II). Primers for sequencing are listed in Table II. Eight to 100 ng of primer were end-labelled with 10 pmol of gamma-P32 labeled ATP (5000 Ci/mmol, 10 µCI/µL) and 5 units of T4 polynucleotide kinase (Promega Biotec) in a 10 µl final volume. Ten ng of primer (1 µl) were added to the sequencing mixture without extraction of unincorporated labelled ATP, boiled for 5 min., and then left at room temperature for ]5 min. Eight units of recombinant Taq polymerase (USB) were added to the mixture. Four µl of the annealed primer/template mixture were later added to 4 µl of each of the stop nucleotide mixes: a) Term mix ddG: 15 microM each dGTP, dATP, dCTP, dTTP; 45 microM ddGTP; b) Term mix ddA: 15 microM each dGTP; dATP; dCTP, dTTP; 600 microM ddATP; c) Term mix ddT: 15 microM each dGTP, dATP, dCTP, dTTP; 1200 microM ddCTP; d) Term mix ddC: 15 microM each dGTP, dATP, dCTP, dTTP; 450 microM ddCTP. The reactions were allowed to proceed for two consecutive periods of 10 min. at 72°–74° C. After the second cycle, each reaction was chased with 2 µl of a 7.5 µM mixture of ATP, GTP, TTP, CTP, and allowed to proceed for 5 min. After spinning down, the reaction was stopped by adding 4 ml of 95% (vol/vol) formamide/20 mM EDTA, heated to 80° C. for 5 min. and loaded on a 0.4 mm thick 6% polyacrylamide/7M urea gel. Electrophoresis was performed at 2500 V for 2 hr, the gel fixed in 5% (vol/vol) glacial acetic acid/5% (v/v) methanol for 15 min, dried, and exposed to Kodak X-Omat film for 4 to 12 hours.

RESULTS

Figure 3:
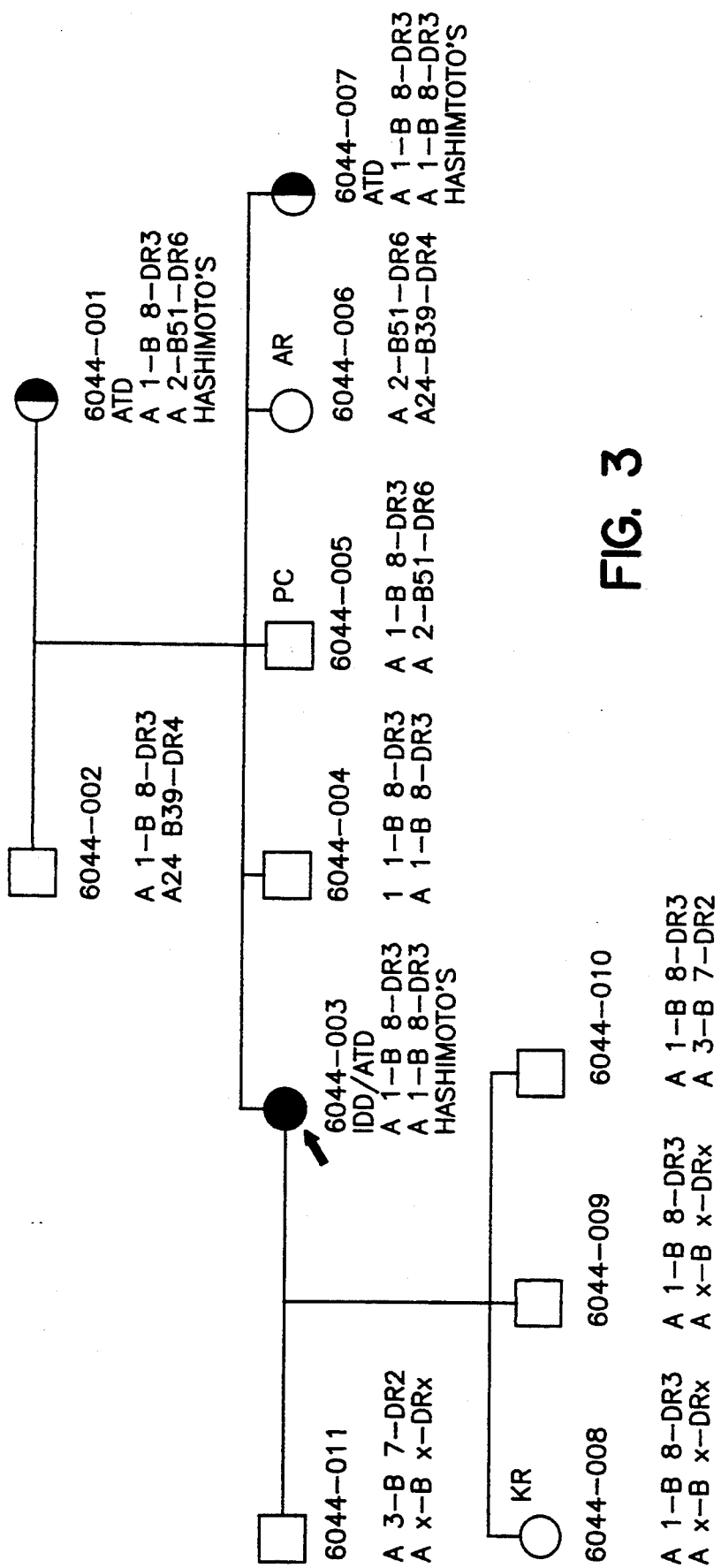
FIG. 3 shows family pedigree of subjects PC, AR and KR as well as their serological typing results for HLA-A, -B and DR loci. Sequence-based Class I typing was not only able to predict the serological reactivities of these subjects, but also to identify new allelic sequences not detectable by serology (i.e., second haplotype of KR).

Optimization of the Sequence-Based Typing of HLA Class I Polymorphic Genes in Heterozygous Cells The designed primers were tested in different combinations in order to generate the desired information (sequence ladders). The optimal combinations of primers and their sequences are shown in Table II. The proposed reactions (1 through 6) are based on their optimization in two heterozygote subjects belonging to the same family that share one of the two chromosomes transmitted from their parents (AR and PC, see Table II and FIG. 3). It was known to the investigator interpreting the sequencing results that these subjects were heterozygotes, but the specific serologic types carried by these individuals were not known to the investigator.

Figure 4A:
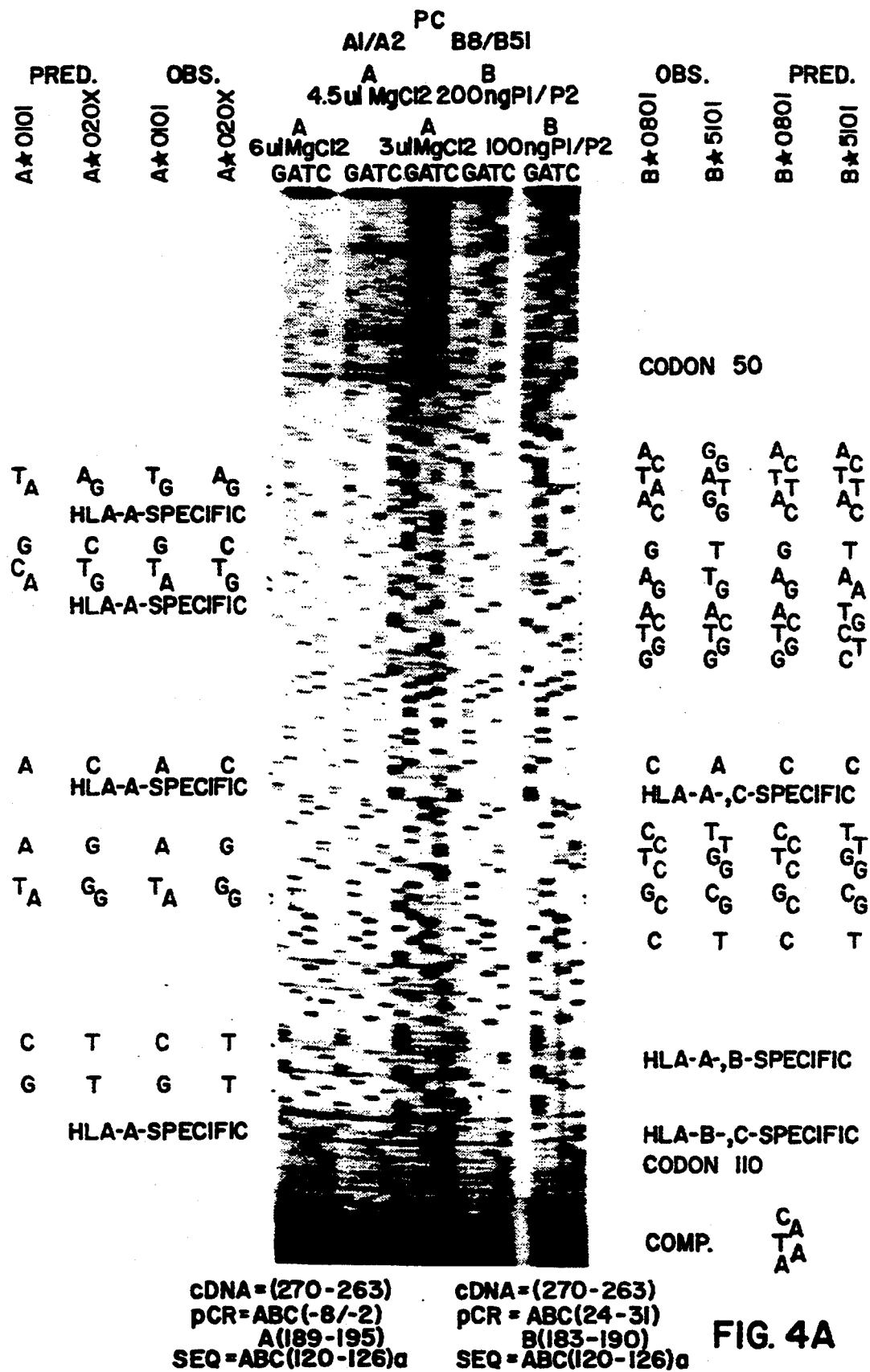
FIGS. 4A and 4B show direct sequencing of A (left) and B (right) genes of subjects PC and AR from family of FIG. 3 using the combination of primers of reactions #2 and #4, respectively. This combination is indicated at the bottom of the Figure. For practical purposes, the template codons to which each of the used primers anneal (i.e., primer ABC101=ABC(−8/−1) are indicated in parenthesis. For the A locus, the Figure shows results obtained by using different $MgCl_2$ concentrations. By decreasing the final $MgCl_2$ concentration (i.e., 3 $\mu$l of 25 mM $MgCl_2$), the reaction results in the selective amplification of one of the two alleles present at the A locus. Increasing the final $MgCl_2$ concentration allows to see the ladders corresponding to each allele without losing the locus-specificity of the reaction. On the side of the Figure, the positions where two bands can be seen or where there should be two bands according to the expected sequences for the serological specificities expressed by these subjects is indicated. The observed (obs.) and expected (pred.) sequences corresponding to each allele at each locus are shown. The locus-specificity of the reactions was assessed by the presence of locus-specific bases at the positions indicated. Codon positions are also indicated as reference points. Comp. means "Compression" and indicates the presence of a sequence artifact at this position due to a compression of bands in the ladder during the electrophoresis. For the B locus, results using two different concentrations of PCR primers (100 ng each or 200 ng each) are shown.
Figure 4B:
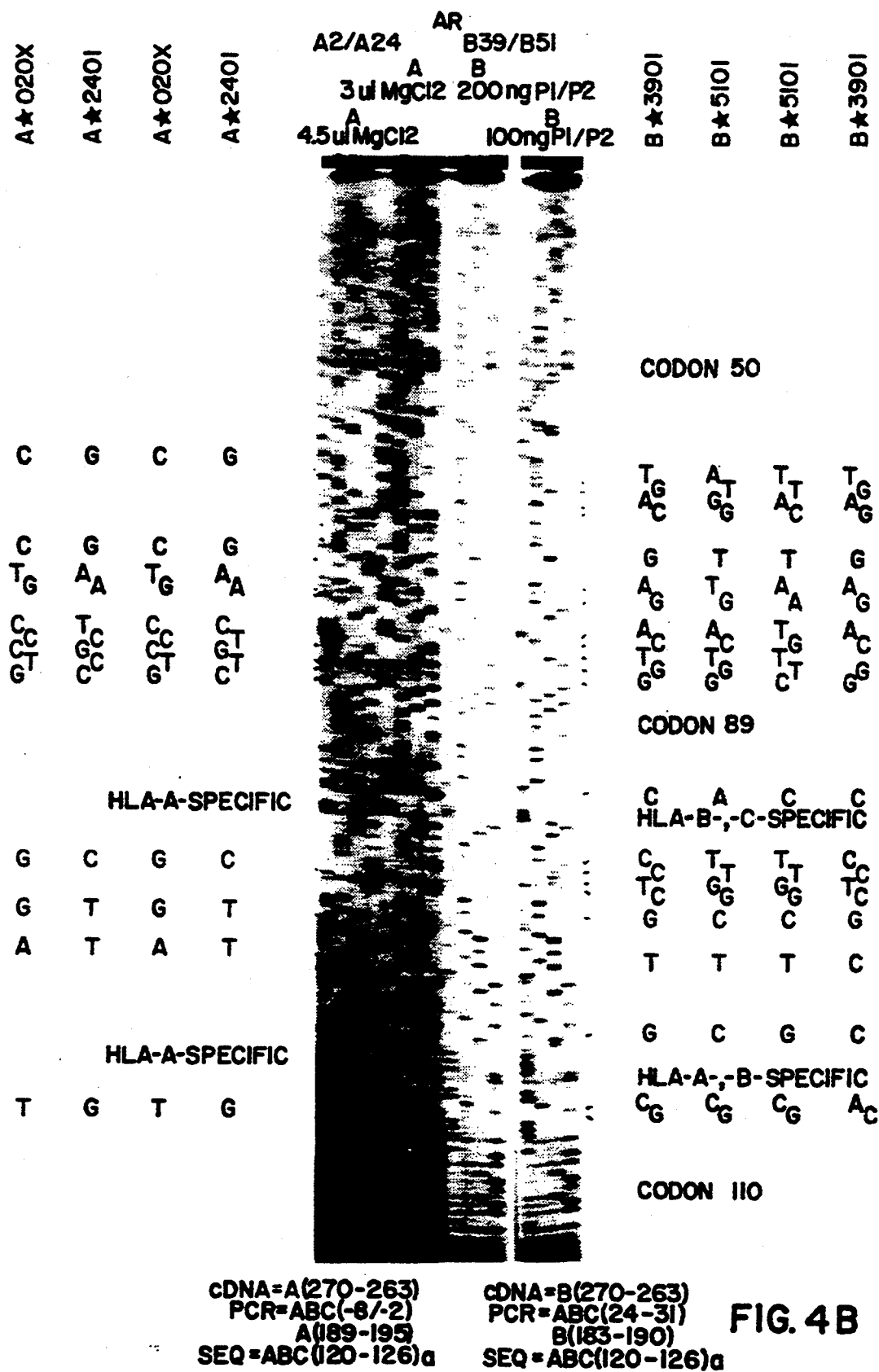
Figure 5:
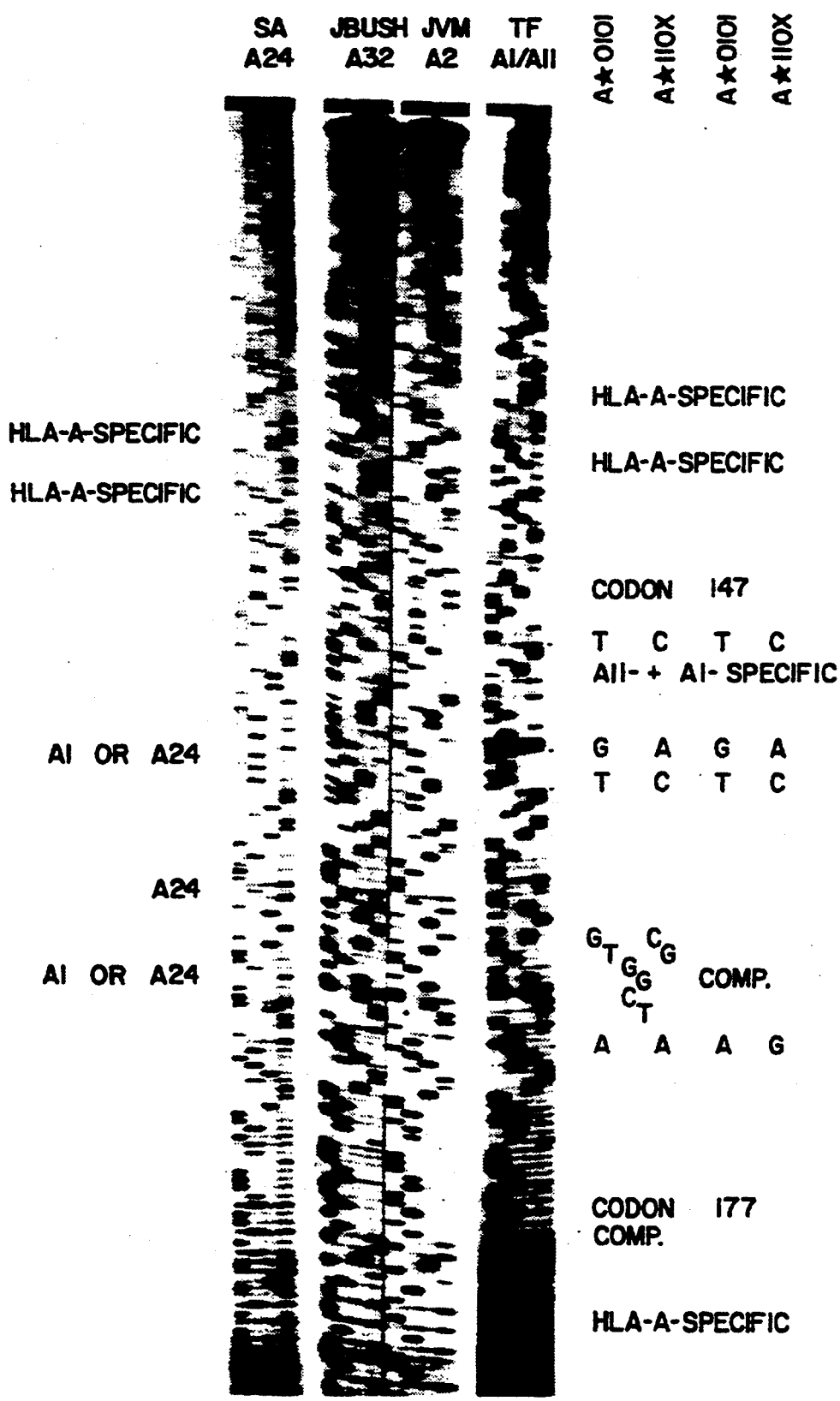
FIG. 5 shows ladders generated for the A locus in 3 homozygous cell lines and a heterozygous subject using combination of primers of reaction #1 (bottom of Figure). Observed and expected sequences are indicated on the side of the Figure for the heterozygote, wherever two bands are either present or expected. Locus- and allele-specific positions, as well as a compression artifact, are also indicated.
Figure 6:
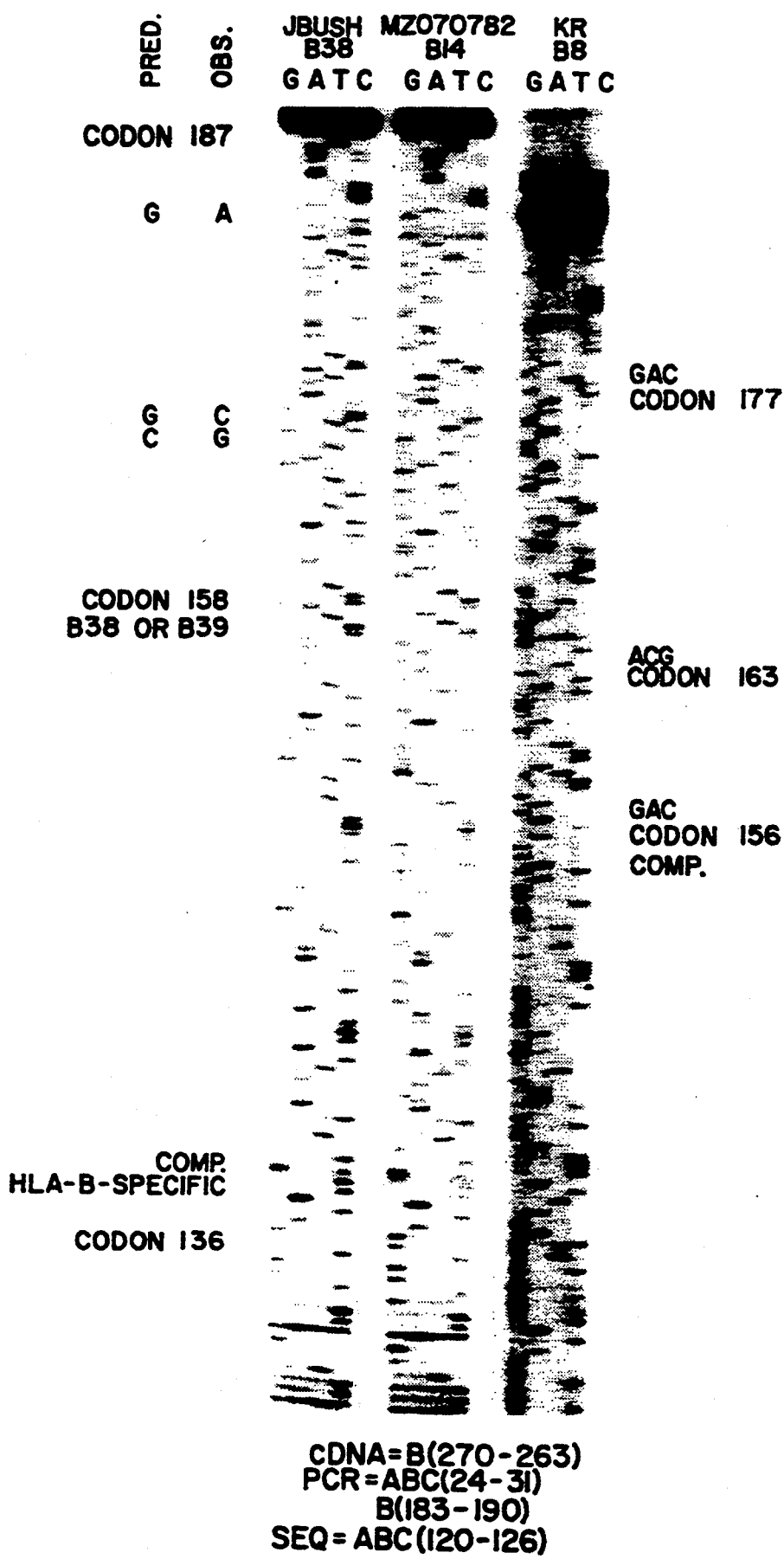
FIG. 6 shows ladders generated for the B locus in two homozygous cell lines and a B locus homozygous subject using conditions of reaction #3. Predicted and expected sequence for specificity B38 (JBUSH cell line) are indicated.

Different primer concentrations, primer combinations including cDNA, PCR and sequencing primers were tested with an initial objective of obtaining locus-specific ladders. The combinations of primers chosen as optimal allowed to obtain locus-specific sequence ladders spanning both of the polymorphic exons of Class I genes. The assessment of the locus-specificity of these reactions was based on the presence of bases in the ladders generated that are found in all known alleles at a given locus, but are absent in all known alleles at the other loci. Examples of such bases are indicated in FIGS. 4, 5 and 6.

A second objective was that such a strategy should allow simultaneous sequencing of both possible alleles at a given locus. For that purpose and knowing that the tested cells were heterozygous at the A and B loci, the conditions of the reactions were optimized accordingly; primer concentrations as well as MgCl$_2$ concentrations in the PCR reaction were modified according. An example of such an experiment is shown in FIG. 4. Note that at 3 or less µl of MgCl$_2$ per PCR reaction, one ladder is selected over the second. By increasing the concentration of MgCl$_2$ per reaction (4–6 µl of 25 mM MgCl$_2$), both alleles are equally amplified without disrupting the locus-specificity of the reaction. Therefore, the optimum conditions are those which provide for clean, reproducible sequencing ladders corresponding to both polymorphic exons and which generate ladders corresponding to at least one and all of the possible alleles carried by any subject at the locus under study (HLA-A or HLA-B or HLA-C). Interpretation of the sequence ladders generated for the A and B loci from both subjects allowed to predict their respective serological reactivities. However, several base-pair substitutions were noted in the alleles carried by these subjects if compared to previously described sequences corresponding to alleles with the same serological reactivities (FIGS. 4–6). Furthermore, family member 6044-008 (same family) who could not be typed completely by serology was sequenced at A and B loci using the strategy described here. Partial sequence analysis of this individual's A and B genes showed that she was heterozygous at the A locus (A*2401/A*0101) but homozygous at the B locus (B*0801) (Table III).

Testing of the "HLA Class I Sequence-Based Typing" Strategy in Serologically-Typed Cell Lines A series of cell lines which had been serologically typed was tested with the optimized strategy, although this serological information was not known to the investigator reading the sequence ladders. The sequence ladder corresponding to each of the performed reactions was first read, compared to known sequences and assigned a serological designation corresponding to the specificity with the highest sequence homology. The results of these experiments are shown in Table III. As shown in Table III, the serological reactivity of the cells could be predicted in all but one case; sequencing of the 3'-end of the third exon of the B genes (encoding the alpha2 domain of the heavy chain of the B antigen) carried by cell line WJR076 indicated that it carried a B*5800 allele. However, serological analysis indicated that it carried a highly related allele: B57 which, in the region sequenced by the corresponding reaction, differs from B58 by a single nucleotide substitution (other differences can be found upstream). This discrepancy could be explained if the sequenced B gene corresponds to a B57 allele that shares its 3' sequence with the B58 allele.

The consanguineous homozygous typing cell RSH (which is supposed to be homozygous at all HLA loci) reacted with A68 and A30 antisera, although the sequence corresponding to the 3' end of the third exon of the A genes corresponded to an A*680x gene. It is possible that upstream portions of the A gene(s) carried by this cell line share sequences with the A30 specificity; in this case, the cell line would be homozygous for a sequence variant of A68 with 5' sequences of an A30 specificity. Interestingly, as indicated in Table III, several new sequence subtypes of A and B specificities were identified with these experiments. The sequencing ladders generated with some of these experiments are shown in FIGS. 4, 5, and 6.

The strategy shown here for Class I HLA typing using SBT (sequence-based typing) can be used to predict the serological reactivity of the typed cells and can detect previously unidentified allelic variants. Furthermore, this approach is inexpensive, requires only 6 cDNA/PCR/Sequencing reactions and allows interpretation of the nucleotide sequences of both polymorphic exons of Class i genes. Thus, this approach can be used as an independent and highly accurate typing method for Class I HLA genes. The Class I HLA typing strategy presented in this application does not require previous typing information and is the only current technique that will allow the most detailed characterization of Class I polymorphism (at the sequence level) in the population.

TABLE III

| Cell Line (WS#) | Serology A | Serology B | Reaction #(*) A | Reaction #(*) B |
|---|---|---|---|---|
| SA (9001) | 24 | 7 | 1 (*2401) | — |
| MZ070782 (9002) | 24 | 14 | 1 (*2401) | 3 (*140x) |
| JBUSH (9035) | 32 | 38 | 1 (*3201) | 3 (*380new) |
| JVM (9039) | 2 | 18 | 1 (*020x) | — |
| BH (9046) | 2 | 13 | 1 (*020x) | 3 (*1301) |
| SAVC (9034) | 3 | 7 | 1 (*0301) | 3 (*070new) |
| DEM (9007) | 2 | 57 | 1 (*020x) | 3 (*5701) |
| WJR076 (9012) | 2 | 57 | 1 (*020x) | 3 (*5801) |
| RML (9016) | 2 | 51 | 1 (*020x) | 3 (*5101) |
| RSH (9021) | 68/30 | 42 | 1 (*680x) | 3 (*4201) |
| HO301 (9055) | 3 | 14 | 1 (*0301) | 3 (*140x) |
| HO301 (9055) | 3 | 14 |  | 4 (*140x) |
| SPOO10 (9036) | 2 | 44 | 1 (*020x) | 3 (*440x) |
| SPOO10 (9036) | 2 | 44 |  | 4 (*4401) |
| KR | 1 | 8 | 1 (*0101 + *2401) | 3 (*0801) |
| TF | 1/11 | 8/7 | 1 (*0101 + *110new) | 3 (*0801 + *0702) |
| (#)PC | 1/2 | 8/51 | 2 (*010new + *020x) | 4 (*080new + *510new) |
| (#)AR | 1/24 | 39/51 | 2 (*020x + *240new) | 4 (*390new + *510new) |

(*) The predicted allele by Sequence-based typing (SBT) are shown in parenthesis: the sequence ladder corresponding to each of the performed reactions was first read, compared to known sequences and assigned a serological designation corresponding to the specificity with the highest sequence homology. The serological results were not known by the investigator interpreting the sequence ladders. The new nomenclature of HLA Class I allelic specificities is used here (for example, the serological A1 allele is designated as A*0101). In some cases, sequence variants have been described for a given serological specificity; these are designated as for example A*1101 and A*1102, etc. In many cases, new sequence variants have been identified by using the method of the present invention and have been designated as "new". If the sequence difference that distinguishes two given variants of a given specificity falls outside the region sequenced in a given reaction, the sequencing results are represented as, for example B*140x (in this particular case the sequence could correspond to either B*1401 or B*1402).
(#) These two subjects are siblings. The new B*51 allelic sequence is shared by both of them as expected; the B allele carried by the second chromosome is different in each subject.
Underlined alleles indicate discrepancy between serological and sequence results. In KR, serological results for Class I genes were incomplete; the second chromosome of this subject could not be typed. However, sequence analysis indicated that the subject was heterozygous at the A locus. Consanguineous cell line RSH was found to be homozygous for A*680x.

EXAMPLE III

Class I Typing Strategy for Determining Unknown HLA Type

Routine HLA typing of large populations of individuals for sequence polymorphisms can be performed by the use of the methodology reported here which can also identify previously unknown allelic variants. FIG. 2 shows a flow-chart for the protocol used to determine sequence allelism of individuals of unknown HLA types.

1. Employment of Primer Combinations for cDNA, PCR and Direct Sequencing Using RNA as Initial Template In the present method, a given Class I typing primer is considered to be "locus-specific" or Class I loci-specific not exclusively on the basis of its nucleotide sequence, but also according to its functional behavior under specific reaction conditions. More specifically, for synthesizing cDNA molecules, the present invention provides single strand DNA anti-sense oligonucleotide primers that anneal to regions relatively conserved (no more than about 2 nucleotide differences) that follow a locus-specific nucleotide sequence pattern of the gene mRNAs to be reverse transcribed, amplified and sequenced. These oligonucleotide primers include an oligonucleotide sequence that: (1) anneals to a region (codons 271-277) shared by the alleles at HLA-A, -B, and -C loci (primer ABC102); (2) anneals to a region (codons 263-270) shared by the alleles at the HLA-A locus (primer A105); (3) anneals to a region (codons 263-270) shared by the alleles at the HLA-B locus (primer B104); (4) anneals to a region (codons 263-270) shared by the alleles at the HLA-C locus. These primers are used in 6 different reactions (1 through 6 in FIG. 2) at a low concentration (10 ng) and are removed by spin-dialysis after the cDNA synthesis reaction in order to increase the functional efficiency of the primers used in the PCR and sequencing reactions. Reactions 1 and 2 are for HLA-A typing, reactions 3 and 4 are for HLA-B typing, and reactions 5 and 6 are for HLA-C typing.

To amplify cDNA molecules corresponding to each Class I locus, two different oligonucleotide primers are added to each reaction. The reactions for each locus generate "locus-specific" amplification under the conditions described in the legend to FIG. 2. Each of these reactions amplify all the alleles carried by any given individual at each separate locus. Each combination of primers will generate information corresponding to only one locus (HLA-A or HLA-B or HLA-C); in heterozygotes at a given locus the sequencing reactions will generate 2 overlapping ladders (each ladder corresponding to each allele at the same locus on each parental chromosome) and in homozygotes only one ladder will be generated (the ladder corresponds to the very same allele at the same locus on both parental chromosomes). These primers are: (1) a sense primer (e.g. ABC109), annealing to codons 24 to 31 of the alleles at all loci (reaction 1); (2) an anti-sense primer (e.g. A105), annealing to codons 270–263 of the alleles at the HLA-A locus (reaction 1); (3) a sense primer (e.g. ABC101), annealing to codons −1 to −8 of the alleles at all loci (reactions 2 through 5); (4) an anti-sense primer (e.g. A108), annealing to codons 189–195 of the alleles at the HLA-A locus (reaction 2); (5) an anti-sense primer (e.g. B107), annealing to codons 184–190 of the alleles at the HLA-B locus (reactions 3 and 4); (6) an anti-sense primer (e.g. C106), annealing to codons 183–190 of the alleles at the HLA-C locus (reactions 5 and 6).

Primers useful in direct sequencing the polymerase-chain reaction products corresponding to Class I HLA loci include: (1) an anti-sense primer (e.g. A108), annealing to codons 189 to 195 of the alleles at HLA-A locus. This primer is used to sequence the products of reaction 1 and generates sequence information corresponding to the alpha2 encoding exon of HLA-A locus; (2) an anti-sense primer (e.g. ABC112), annealing to codons 120 to 126 of the alleles at all Class I loci. This primer is used to sequence the products of reactions 2 (HLA-A), 4 (HLA-B) and 6 (HLA-C) and generates sequence information for the 5' end of the alpha2-encoding exon and all the alpha1-encoding exon of Class I genes; (3) a sense primer (e.g. ABC113), annealing to codons 120 to 126 of the alleles at all Class I loci. This primer is used for sequencing the products of reactions 3 (HLA-B) and 5 (HLA-C) and generates sequence information for the 3'-end of the alpha2-encoding exon of the corresponding Class I genes.

2. Procedure for Determining Unknown HLA Type

A subject of unknown HLA type, diseased or not, is to be typed for Class I HLA polymorphism. From 10 to 50 mL of peripheral blood are drawn. The peripheral blood mononuclear cells are prepared by centrifugation over Ficoll-Hypaque gradients. The cells are then lysed in guanidium isothyocianate and total cellular RNA prepared using conventional methods (either by centrifugation on cesium chloride gradients, which lasts about 16 hours, or by the guanidium isothyocianate-phenol-chlorophorm extraction method, which can be performed in less than 4 hours. See Gouuh, supra (1988); Johns et al., Anal, Biochem., 180:276 (1989). Otherwise genomic DNA from these cells or other sources (hair, blood stains, sperm, etc.) can be prepared with conventional methods such as provided by Higuchi, R. in PCR Technology, Erlich, M. (ed.), Stockton Press:31 (1989). HLA-A/B/C, HLA-A, HLA-B, and HLA-C cDNA molecules are synthesized from total RNA using locus-specific primers. Approximately, one to five micrograms of RNA is reverse transcribed with MoLVRT (reverse transcriptase) and HLA-A, -B, and -C loci, HLA-A (A105 and/or ABC102), HLA-B (B104) and HLA-C (C103), -specific anti-sense primers in a 20 $\mu$l final volume reaction (30–60 minute incubation). The reaction for each Class I gene is performed in a different tube.

Once these reactions are completed, they are spin dialyzed to remove unincorporated reverse transcriptase primer, and the enzymatic amplification of the respective cDNA molecules is then performed by adding to the retentate of the spin-dialysis, the reagents needed for the amplification step. This includes the PCR reagents and appropriate combination of Class I loci-specific and individual locus-specific oligonucleotide primers. This example uses two reactions for HLA-A (tubes 1 and 2), two for HLA-B (tubes 3 and 4), and two for HLA-C (tubes 5 and 6). Reactions 1 and 2 incorporate primers ABC109 and A105 or ABC101 and A108, respectively. Tubes 3 and 4 incorporate primer B107 and ABC109 or B107 and ABC101, respectively, and tubes 5 and 6 incorporate primer C106 and ABC109 or C106 and ABC101, respectively, Once completed, the reactions are spun-dialyzed for about 15 minutes using Ultrafree-100 (Millipore) or similar columns to remove unincorporated primers and dNTPs. The retentate or one half of the recovered retentate for each reaction is then directly sequenced using Taq polymerase and the primers described in Table II for each combination of primers used in the cDNA/PCR reactions using P-32 end-labeled (10 minutes) sequencing primers (35 minutes).

The sequencing reactions products are loaded on an acrylamide gel, electrophoresed in 2–3 hours and exposed to X-ray films for 4–12 hours. The gels are read and results from gels are compared to nucleotide sequences corresponding to all possible alleles.

Comparisons can be made visually using the naked eye or using a personal computer and a software package including the nucleotide sequences of all alleles of all haplotypes and routines which indicate how the comparison is to be performed as well as subroutines which will allow identification of new allelic sequences.

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear (i i) MOLECULE TYPE: Genomic DNA (i v) ANTI-SENSE: no (v) FRAGMENT TYPE: Internal Fragment (v i) ORIGINAL SOURCE: Synthetically Derived (i x) FEATURE:
    (A) NAME/KEY: Oligonucleotide Primer ABC101
    (B) LOCATION: Anneals to codons -8 to -1 of the
        A, B and C transcripts of HLA class I (x i) SEQUENCE DESCRIPTION: SEQ ID NO: 1:

```
     G  GCC  CTG  ACC  GAG  ACC  TGG  GC              21
        Ala  Leu  Thr  Glu  Thr  Trp  Ala
             -5                      -1
```

(2) INFORMATION FOR SEQ ID NO: 2:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (i i) MOLECULE TYPE: Genomic DNA (i v) ANTI-SENSE: yes (v) FRAGMENT TYPE: Internal Fragment (v i) ORIGINAL SOURCE: Synthetically Derived (i x) FEATURE:
    (A) NAME/KEY: Oligonucleotide Primer ABC102
    (B) LOCATION: Anneals to codons 271 to 277 of the
        A, B and C transcripts of HLA class I (x i) SEQUENCE DESCRIPTION: SEQ ID NO: 2:

```
        AGA  TGG  CTC  CCA  TCT  CAG  GGT           21
```

(2) INFORMATION FOR SEQ ID NO: 3:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (i i) MOLECULE TYPE: Genomic DNA (i v) ANTI-SENSE: yes (v) FRAGMENT TYPE: Internal Fragment (v i) ORIGINAL SOURCE: Synthetically Derived (i x) FEATURE:
    (A) NAME/KEY: Oligonucleotide Primer C103
    (B) LOCATION: Anneals to codons 263 to 270 of the
        C transcript of HLA class I (x i) SEQUENCE DESCRIPTION: SEQ ID NO: 3:

```
        AGG  GGC  TCT  GGC  AGC  CCC  TCG           21
```

(2) INFORMATION FOR SEQ ID NO: 4:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (i i) MOLECULE TYPE: Genomic DNA (i v) ANTI-SENSE: yes (v) FRAGMENT TYPE: Internal Fragment (v i) ORIGINAL SOURCE: Synthetically Derived (i x) FEATURE:
- (A) NAME/KEY: Oligonucleotide Primer B104
- (B) LOCATION: Anneals to codons 263 to 270 of the B transcript of HLA class I (x i) SEQUENCE DESCRIPTION: SEQ ID NO: 4:

```
          AGG GGC TTC GGC AGC CCC TCA                    21
```

(2) INFORMATION FOR SEQ ID NO: 5:

(i) SEQUENCE CHARACTERISTICS:
- (A) LENGTH: 21 base pairs
- (B) TYPE: Nucleic Acid
- (C) STRANDEDNESS: Single
- (D) TOPOLOGY: Linear (i i) MOLECULE TYPE: Genomic DNA (i v) ANTI-SENSE: yes (v) FRAGMENT TYPE: Internal Fragment (v i) ORIGINAL SOURCE: Synthetically Derived (i x) FEATURE:
- (A) NAME/KEY: Oligonucleotide Primer A105
- (B) LOCATION: Anneals to codons 263 to 270 of the A transcript of HLA class I (x i) SEQUENCE DESCRIPTION: SEQ ID NO: 5:

```
          AGG GGC TTG GGC AGA CCC TCA                    21
```

(2) INFORMATION FOR SEQ ID NO: 6:

(i) SEQUENCE CHARACTERISTICS:
- (A) LENGTH: 21 base pairs
- (B) TYPE: Nucleic Acid
- (C) STRANDEDNESS: Single
- (D) TOPOLOGY: Linear (i i) MOLECULE TYPE: Genomic DNA (i v) ANTI-SENSE: yes (v) FRAGMENT TYPE: Internal Fragment (v i) ORIGINAL SOURCE: Synthetically Derived (i x) FEATURE:
- (A) NAME/KEY: Oligonucleotide Primer C106
- (B) LOCATION: Anneals to codons 183 to 190 of the C transcript of HLA class I (x i) SEQUENCE DESCRIPTION: SEQ ID NO: 6:

```
          GTC ACG TGT GTC TTT GGG TGT                    21
```

(2) INFORMATION FOR SEQ ID NO: 7:

(i) SEQUENCE CHARACTERISTICS:
- (A) LENGTH: 21 base pairs
- (B) TYPE: Nucleic Acid
- (C) STRANDEDNESS: Single
- (D) TOPOLOGY: Linear (i i) MOLECULE TYPE: Genomic DNA (i v) ANTI-SENSE: yes (v) FRAGMENT TYPE: Internal Fragment (vi) ORIGINAL SOURCE: Synthetically Derived (ix) FEATURE:
    (A) NAME/KEY: Oligonucleotide Primer B107
    (B) LOCATION: Anneals to codons 184 to 190 of the
        B transcript of HLA class I (xi) SEQUENCE DESCRIPTION: SEQ ID NO: 7:

```
     GGT CAC ATG TGT CTT TGG GGG                    21
```

(2) INFORMATION FOR SEQ ID NO: 8:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: yes (v) FRAGMENT TYPE: Internal Fragment (vi) ORIGINAL SOURCE: Synthetically Derived (ix) FEATURE:
        (A) NAME/KEY: Oligonucleotide Primer A108
        (B) LOCATION: Anneals to codons 189 to 195 of the
            A transcript of HLA class I (xi) SEQUENCE DESCRIPTION: SEQ ID NO: 8:

```
     AGA GAT AGC GTG GTG GGT CAT                    21
```

(2) INFORMATION FOR SEQ ID NO: 9:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: no (v) FRAGMENT TYPE: Internal Fragment (vi) ORIGINAL SOURCE: Synthetically Derived (ix) FEATURE:
        (A) NAME/KEY: Oligonucleotide Primer ABC109
        (B) LOCATION: Anneals to codons 24 to 31 of the
            A, B and C transcripts of HLA class I (xi) SEQUENCE DESCRIPTION: SEQ ID NO: 9:

```
     CA GTG GGC TAC GTG GAC GAC A                   21

Val Gly Tyr Val Asp Asp
        25                   30
```

(2) INFORMATION FOR SEQ ID NO: 10:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (ii) MOLECULE TYPE: Genomic DNA (iv) ANTI-SENSE: yes (v) FRAGMENT TYPE: Internal Fragment -continued ( v i ) ORIGINAL SOURCE: Synthetically Derived ( i x ) FEATURE:
    ( A ) NAME/KEY: Oligonucleotide Primer ABC116
    ( B ) LOCATION: Anneals to codons 33 to 39 of the
        A, B and C transcripts of HLA class I ( x i ) SEQUENCE DESCRIPTION: SEQ ID NO: 10:

GTC GCT GTC GAA CCT CAC GAA    21

( 2 ) INFORMATION FOR SEQ ID NO: 11:

( i ) SEQUENCE CHARACTERISTICS:
        ( A ) LENGTH: 20 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: yes ( v ) FRAGMENT TYPE: Internal Fragment ( v i ) ORIGINAL SOURCE: Synthetically Derived ( i x ) FEATURE:
        ( A ) NAME/KEY: Oligonucleotide Primer ABC112
        ( B ) LOCATION: Anneals to codons 121 to 127 of the
            A, B and C transcripts of HLA class I ( x i ) SEQUENCE DESCRIPTION: SEQ ID NO: 11:

TT CAG GGC GAT GTA ATC CTT    20

( 2 ) INFORMATION FOR SEQ ID NO: 12:

( i ) SEQUENCE CHARACTERISTICS:
        ( A ) LENGTH: 21 base pairs
        ( B ) TYPE: Nucleic Acid
        ( C ) STRANDEDNESS: Single
        ( D ) TOPOLOGY: Linear ( i i ) MOLECULE TYPE: Genomic DNA ( i v ) ANTI-SENSE: no ( v ) FRAGMENT TYPE: Internal Fragment ( v i ) ORIGINAL SOURCE: Synthetically Derived ( i x ) FEATURE:
        ( A ) NAME/KEY: Oligonucleotide Primer ABC113
        ( B ) LOCATION: Anneals to codons 120 to 126 of the
            A, B and C transcripts of HLA class I ( x i ) SEQUENCE DESCRIPTION: SEQ ID NO: 12:

GGC AAG GAT TAC ATC GCC CTG    21
    Gly Lys Asp Try Ile Ala Leu
    120                125

What is claimed:

1. A method for determining a nucleotide sequence of a Class I HLA-A gene locus of a subject in a sample containing subject RNA, said method comprising:
(a) synthesizing, from RNA isolated from said sample, a cDNA molecule for each allele of said gene locus using in a first synthesis reaction an oligonucleotide primer depicted in SEQ. ID NO: 2 to produce a first cDNA molecule and in a second synthesis reaction an oligonucleotide primer depicted in SEQ. ID NO:5 to produce a second cDNA molecule, wherein in said first and second synthesis reactions said primer is present in a limiting amount;
(b) amplifying said first and second cDNA molecules to generate sufficient first and second double stranded amplification reaction products respectively for sequencing each allele of said gene locus using in the first amplifying reaction an oligonucleotide primer depicted in SEQ. ID. NO:9 and an oligonucleotide primer depicted in SEQ. ID. NO:5 and in the second amplifying reaction an oligonucleotide primer depicted in SEQ. ID. NO:I and an oligonucleotide primer depicted in SEQ. ID. NO:8;

(c) sequencing directly each first and second amplification reaction product to produce two sequencing ladders for each amplification reaction product using in the first sequencing reaction an oligonucleotide primer depicted in SEQ. ID. NO:8 and in the second sequencing reaction an oligonucleotide primer depicted in SEQ. ID. NO:11; and (d) analyzing each sequencing ladder to determine the nucleotide sequence of said HLA-A gene locus.

2. The method according to claim 1, wherein said primer depicted in SEQ. ID. NO:5 is present in said first amplifying reaction in a limiting amount so that it is consumed in said reaction.

3. A method for determining a nucleotide sequence of a Class I HLA-B gene locus of a subject in a sample containing subject RNA, said method comprising:

(a) synthesizing, from RNA isolated from said sample, a cDNA molecule for each allele of said gene locus using in a first synthesis reaction an oligonucleotide primer depicted in SEQ. ID NO:4 to produce a first cDNA molecule and in a second synthesis reaction an oligonucleotide primer depicted in SEQ. ID. NO:4 to produce a second cDNA molecule, wherein in said first and second synthesis reactions said primer is present in a limiting amount;

(b) amplifying said first and second cDNA molecules to generate sufficient first and second double stranded amplification reaction products respectively for sequencing each allele of said gene locus using in the first amplifying reaction an oligonucleotide primer depicted in SEQ. ID. NO:9 and an oligonucleotide primer depicted in SEQ. ID. NO:7 and in the second amplifying reaction an oligonucleotide primer depicted in SEQ. ID. NO:I and an oligonucleotide primer depicted in SEQ. ID. NO:7;

(c) sequencing directly each first and second amplification reaction product to produce two sequencing ladders for each amplification reaction product using in the first sequencing reaction an oligonucleotide primer depicted in SEQ. ID. NO:12 and in the second sequencing reaction an oligonucleotide primer depicted in SEQ. ID. NO:11; and (d) analyzing each sequencing ladder to determine the nucleotide sequence of said HLA-B gene locus.

4. A method for determining a nucleotide sequence of a Class I HLA-C gene locus of a subject in a sample containing subject RNA, said method comprising:

(a) synthesizing, from RNA isolated from said sample, a cDNA molecule for each allele of said gene locus using in a first synthesis reaction an oligonucleotide primer depicted in SEQ. ID NO:3 to produce a first cDNA molecule and in a second synthesis reaction an oligonucleotide primer depicted in SEQ. ID. NO:3 to produce a second cDNA molecule, wherein in said first and second synthesis reactions said primer is present in a limiting amount;

(b) amplifying said first and second cDNA molecules to generate sufficient first and second double stranded amplification reaction products respectively for sequencing each allele of said gene locus using in the first amplifying reaction an oligonucleotide primer depicted in SEQ. ID. NO:9 and an oligonucleotide primer depicted in SEQ. ID. NO:6 and in the second amplifying reaction an oligonucleotide primer depicted in SEQ. ID. NO:i and an oligonucleotide primer depicted in SEQ. ID. NO:6;

(c) sequencing directly each first and second amplification reaction product to produce two sequencing ladders for each amplification reaction product using in the first sequencing reaction an oligonucleotide primer depicted in SEQ. ID. NO:12 and in the second sequencing reaction an oligonucleotide primer depicted in SEQ. ID. NO:11; and (d) analyzing each sequencing ladder to determine the nucleotide sequence of said HLA-C gene locus.

5. A method as in any of claims 1-4, for rapid automated determination of HLA Class I genotype of a subject in a sample containing subject nucleic acid wherein:

(a) said RNA is isolated from said sample with an RNA/DNA extractor;

(b) said amplifying reactions are done using a thermocycler;

(c) said sequencing is done using an automated sequencing apparatus; and (d) said analyzing each sequencing ladder to determine the nucleotide sequence of each gene locus of interest of said subject is done with a computer having a data base with allelic sequence information to compare the sequence of each allele of each gene locus sequenced to known sequences for each gene locus of interest, wherein said gene locus is selected from the group consisting of HLA-A, HLA-B, and HLA-C.

6. An oligonucleotide primer having the sequence depicted in SEQ. ID NO: 2.

7. An oligonucleotide primer having the sequence depicted in SEQ. ID NO:3.

8. An oligonucleotide primer having the sequence depicted in SEQ. ID NO:4.

9. An oligonucleotide primer having the sequence depicted in SEQ. ID NO:5.

10. An oligonucleotide primer having the sequence depicted in SEQ. ID NO:6.

11. An oligonucleotide primer having the sequence depicted in SEQ. ID NO:7.

12. An oligonucleotide primer having the sequence depicted in SEQ. ID NO: 8.

13. An oligonucleotide primer having the sequence depicted in SEQ. ID NO:9.

14. An oligonucleotide primer having the sequence depicted in SEQ. ID NO:10.

* * * * *